(12) United States Patent
Jimenez et al.

(10) Patent No.: US 10,752,896 B2
(45) Date of Patent: Aug. 25, 2020

(54) SIRNA AND THEIR USE IN METHODS AND COMPOSITIONS FOR INHIBITING THE EXPRESSION OF THE NRARP GENE

(71) Applicant: SYLENTIS SAU, Madrid (ES)

(72) Inventors: Ana Isabel Jimenez, Madrid (ES); Covadonga Pañeda, Madrid (ES); Tamara Martinez, Madrid (ES)

(73) Assignee: SYLENTIS SAU, Madrid (ES)

( * ) Notice: Subject to any disclaimer, the term of this patent is extended or adjusted under 35 U.S.C. 154(b) by 0 days.

(21) Appl. No.: 15/757,051

(22) PCT Filed: Sep. 7, 2016

(86) PCT No.: PCT/EP2016/071122
§ 371 (c)(1),
(2) Date: Mar. 2, 2018

(87) PCT Pub. No.: WO2017/042238
PCT Pub. Date: Mar. 16, 2017

(65) Prior Publication Data
US 2018/0340177 A1    Nov. 29, 2018

(30) Foreign Application Priority Data
Sep. 8, 2015  (EP) .................................... 15382440

(51) Int. Cl.
*C12N 15/113*  (2010.01)
*A61P 27/02*   (2006.01)

(52) U.S. Cl.
CPC ............ *C12N 15/113* (2013.01); *A61P 27/02* (2018.01); *C12N 2310/14* (2013.01); *C12N 2310/315* (2013.01); *C12N 2310/32* (2013.01); *C12N 2310/321* (2013.01); *C12N 2310/3235* (2013.01); *C12N 2310/335* (2013.01); *C12N 2310/344* (2013.01)

(58) Field of Classification Search
CPC .............. C12N 15/113; C12N 2310/14; C12N 2310/31; C12N 2310/32; A01K 2207/05
See application file for complete search history.

(56) References Cited

U.S. PATENT DOCUMENTS

| | | | |
|---|---|---|---|
| 6,506,559 B1 * | 1/2003 | Fire | A61K 31/7105 435/325 |
| 2005/0202428 A1 * | 9/2005 | Andrews | C12N 5/0606 435/6.14 |
| 2005/0246794 A1 * | 11/2005 | Khvorova | A61K 31/713 800/286 |
| 2013/0123330 A1 | 5/2013 | Lu et al. | |
| 2013/0130377 A1 | 5/2013 | Lee et al. | |

FOREIGN PATENT DOCUMENTS

| | | | |
|---|---|---|---|
| EP | 2322617 | 6/2014 | |
| EP | 2348133 | 7/2014 | |
| EP | 1527176 | 2/2017 | |
| WO | WO 02/44321 | 6/2002 | |
| WO | WO-2004060304 A2 * | 7/2004 | ............ C07K 14/47 |
| WO | WO 2005/062937 | 7/2005 | |
| WO | WO 2008/050329 | 5/2008 | |
| WO | WO 2008/104978 | 9/2008 | |
| WO | WO 2009/044392 | 4/2009 | |
| WO | WO 2010/048352 | 4/2010 | |
| WO | WO 2015/059116 | 4/2015 | |
| WO | WO 2015/059122 | 4/2015 | |
| WO | WO 2015/059124 | 4/2015 | |

OTHER PUBLICATIONS

Guzman-Aranguez et al., "Small-Interfering RNAs (siRNAs) as a Promising Tool for Ocular Therapy," British Journal of Pharmacology, vol. 170, pp. 730-747, 2013.
Imaoka et al., "Overexpression of NOTCH-regulated Ankyrin Repeat Protein is Associated with Breast Cnacer Cell Proliferation," Anticancer Research, vol. 34, pp. 2165-2172, 2014.
Lobov, et al., "The Dll4/Notch Pathway Controls Postangiogenic Blood Vessel Remodeling and Regression by Modulating Vasoconstriction and Blood Flow," Blood, vol. 117, No. 24, pp. 6728-6737, 2011.
Phng et al., "Nrarp Coordinates Endothelial Notch and Wnt Signaling to Control Vessel Density in Angiogenesis," Developmental Cell, vol. 16, pp. 70-82, 2009.
Sylentis SAU, International Preliminary Report on Patentability for PCT/EP2016/071122, 7 pages, dated Mar. 13, 2018.
Angaji et al., "Application of RNA interference in treating human diseases" J Genet. 2010. vol. 89. 4. pp. 527-537.
Bird AC. "Therapeutic targets in age-related macular disease". J Clin Invest. Sep. 2010; 120 (9) :3033-41.
Bramsen J.B., Laursen M.B., Nielsen A. F., et al. "A large-scale chemical modification screen identifies design rules to generate siRNAs with high activity, high stability and low toxicity", Nucleic Acids Res 2009 vol. 37 Issue: 9 pp. 2867-2881.
PA Campochiaro, "Potential applications for RNAi to probe pathogenesis and develop new treatments for ocular disorders". Gene Ther. Mar. 2006; 13 (6) :559-62.
Cerutti, L., N. Mian, et al. "Domains in gene silencing and cell differentiation proteins: the novel PAZ domain and redefinition of the Piwi domain." Trends Biochem Sci. 2000 25(10): 481-2.
Collins, R. E. and X. Cheng. "Structural domains in RNAi." FEBS Lett 2005 579(26): 5841-5849.

(Continued)

*Primary Examiner* — Brian Whiteman
(74) *Attorney, Agent, or Firm* — King & Spalding LLP

(57) ABSTRACT

The invention relates to si RNA molecules and their use in methods and pharmaceutical compositions for inhibiting the expression of the NRARP gene. The invention also relates to the use of said si RNAs molecules in the treatment and/or prevention of a disease or disorder related to neovascularization characterised by increased expression and/or activity of NRARP gene, said eye condition is selected from the group comprising age-related macular degeneration (AMD), ischemic retinopathy, diabetic macular edema (DME), proliferative diabetic retinopathy (PDR), diabetic retina ischemia (DRI), diabetic retinal edema (DRE) and retinopathy of prematurity (ROP) and combinations thereof.

26 Claims, 19 Drawing Sheets
Specification includes a Sequence Listing.

(56) References Cited

OTHER PUBLICATIONS

Chang C.I, Kim H.A, Dua P, et al. "Structural Diversity Repertoire of Gene Silencing Small Interfering RNAs" Nucleic Acid Ther. 2011. vol. 21. 3. pp. 125-131.

Chong RH, et al., "Gene silencing following siRNA delivery to skin via coated steel microneedles: in vitro and in vivo proof-of-concept", *J Control Release*, Mar. 28, 2013, pp. 1-20, 166(3).

Del Amo et al., "Current and future ophthalmic drug delivery systems A shift to the posterior segment", Drug Discovery Today, Feb. 2008, pp. 135-143, vol. 13.

Deleavey et al., "Designing Chemically Modified Oligonucleotides for Targeted Gene Silencing", Chemistry & Biology 19, Aug. 24, 2012, pp. 937-954.

Doench, et al., "Specificity of microRNA target selection in translational repression", Genes & Development, 2004, pp. 504-511.

Duvvuri et al., "Drug delivery to the retina: challenges and opportunities", *Expert Opin Biol. Ther.*, 2003, pp. 45-56, 3(7).

Edelhauser et al., "Ophthalmic Drug Delivery Systems for the Treatment of Retinal Diseases: Basic Research to Clinical Applications", Investigative Ophthalmology & Visual Science, Nov. 2010, pp. 5403-5420, vol. 51, No. 11.

Elbashir et al., "RNA interference is mediated by 21- and 22-nucleotide RNAs", Genes & Development, 2001, pp. 188-200, 15.

Faibish et al., "A YKL-40-Neutralizing Antibody Blocks Tumor Angiogenesis and Progression: A Potential Therapeutic Agent in Cancers",*Molecular Cancer Therapeutics*, 2011, pp. 742-751, 10(5).

Fire et al., "Potent and specific genetic interference by double-stranded RNA in Caenorhabditis elegans", Nature, 1998, pp. 806-811, vol. 391.

Grossniklaus et al., "Animal Models of Choroidal and Retinal Neovascularization", Prog Retin Eye Res., Nov. 2010, pp. 500-519, 29(6).

Guzman-Aranguez et al., "Small-interfering RNAs (siRNAs) as a promising tool for ocular therapy", British Journal of Pharmacology, (2013), pp. 730-747, 170.

Hernandez et al., "A highly efficient electroporation method for the transfection of endothelial cells", Angiogenesis, 2004, pp. 235-241, 7.

Hutvagner, et al., A microRNA in a Multiple-Turnover RNAi Enzyme Complex, Science, 2002, pp. 2056-2060, vol. 297.

Kigasawa, K., et al., "Noninvasive delivery of siRNA into the epidermis by iontophoresis using an atopic dermatitis-like model rat", International Journal of Pharmaceutics, (2009), pp. 1-4.

Kim et al., "Synthetic dsRNA Dicer substrates enhance RNAi potency and efficacy", Nature Biotechnology, 2005, pp. 222-226, vol. 23, No. 2.

Kornbrust, et al., "Oligo Safety Working Group Exaggerated Pharmacology Subcommittee Consensus Document", Nucleic Acid Therapeutics, 2013, pp. 21-29, vol. 23, No. 1.

Leachman, et al., "First-in-human Mutation-targeted siRNA Phase Ib Trial of an Inherited Skin Disorder", Molecular Therapy, 2010, pp. 442-446, vol. 18 No. 2.

Lewis, et al., "Prediction of Mammalian MicroRNA Targets", Cell Dec. 26, 2003, pp. 787-798, vol. 115.

Liu, et al., "Argonaute2 Is the Catalytic Engine of Mammalian RNAi", Science, Sep. 3, 2004, pp. 1437-1441, vol. 305.

Livak, et al., "Analysis of Relative Gene Expression Data Using Real-Time Quantitative PCR and the 2-♦♦ CT Method", Methods, 2001, pp. 402-408, 25.

Ma, et al.,"Structural basis for 5'-end-specific recognition of guide RNA by the *A. fulgidus* Piwi protein", *Nature*, Mar. 31, 2005, pp. 666-670, 434(7033).

Maniatis, et al., "Separation of RNA According to Size: Electrophoresis of Glyoxylated RNA through Agarose Gels", Molecular Cloning, file:///H|/TEMP/Protocols/7P5.htm (4 of 5), 2000, pp. 1-5.

Nakai, et al., "Therapeutic RNA interference of malignant melanoma by electrotransfer of small interfering Rna targeting Mitf", Gene Therapy, (2007), pp. 357-365, 14.

Nykanen, et al., "ATP Requirements and Small Interfering RNA Structure in the RNA Interference Pathway", Cell, Nov. 2, 2001, pp. 309-321, vol. 107.

Orban, et al., "Decay of mRNAs targeted by RISC requires XRN1, the Ski complex, and the exosome," *RNA* (2005), pp. 459-469, vol. 11, No. 4.

Parrish, et al., "Functional Anatomy of a dsRNA Trigger: Differential Requirement for the Two Trigger Strands in RNA Interference", Molecular Cell, Nov. 2000, pp. 1077-1087, vol. 6.

Phng, et al., "Nrarp Coordinates Endothelial Notch and Wnt Signaling to Control Vessel Density in Angiogenesis", Developmental Cell 16, Jan. 20, 2009, pp. 70-82.

Rand, et al., "Argonaute2 Cleaves the Anti-Guide Strand of siRNA during RISC Activation", Cell, Nov. 18, 2005, pp. 621-629, vol. 123.

Rowe-Rendleman, et al., "Drug and Gene Delivery to the Back of the Eye: From Bench to Bedside", *IOVS*, Apr. 2014, pp. 2714-2730, vol. 55, No. 4.

Sanghvi, "A Status Update of Modified Oligonucleotides for Chemotherapeutics Applications", Current Protocols in Nucleic Acid Chemistry, Sep. 2011, pp. 4.1.1-4.1.22.

Song, et al., "Crystal Structure of Argonaute and Its Implications for RISC Slicer Activity", Science, Sep. 3, 2004, pp. 1434-1437, Vo. 305 (5689).

Walton, et al., "Designing highly active siRNAs for therapeutic applications", FEBS Journal 277, (2010) pp. 4806-4813.

\* cited by examiner

| NRARP target sequences (cDNA) | |
|---|---|
| SEQ ID NO. 1 | CACCAGGACATCGTGCTCT |
| SEQ ID NO. 2 | ACATCGTGCTCTATCTCAT |
| SEQ ID NO. 3 | AGGACATCGTGCTCTATCT |
| SEQ ID NO. 4 | GACATCGTGCTCTATCTCA |
| SEQ ID NO. 5 | TGCTCTATCTCATCACCAA |
| SEQ ID NO. 6 | CCAGGACATCGTGCTCTAT |
| SEQ ID NO. 7 | ATCGTGCTCTATCTCATCA |
| SEQ ID NO. 8 | GTGCTCTATCTCATCACCA |
| SEQ ID NO. 9 | ACCAGGACATCGTGCTCTA |

FIGURE 1

| NRARP siRNAs | Sense strand 5´->3´ | Antisense strand 5´->3´ |
|---|---|---|
| SEQ ID NO. 10 | CACCAGGACAUCGUGCUCU | AGAGCACGAUGUCCUGGUG |
| SEQ ID NO. 11 | ACAUCGUGCUCUAUCUCAU | AUGAGAUAGAGCACGAUGU |
| SEQ ID NO. 12 | AGGACAUCGUGCUCUAUCU | AGAUAGAGCACGAUGUCCU |
| SEQ ID NO. 13 | GACAUCGUGCUCUAUCUCA | UGAGAUAGAGCACGAUGUC |
| SEQ ID NO. 14 | UGCUCUAUCUCAUCACCAA | UUGGUGAUGAGAUAGAGCA |
| SEQ ID NO. 15 | CCAGGACAUCGUGCUCUAU | AUAGAGCACGAUGUCCUGG |
| SEQ ID NO. 16 | AUCGUGCUCUAUCUCAUCA | UGAUGAGAUAGAGCACGAU |
| SEQ ID NO. 17 | GUGCUCUAUCUCAUCACCA | UGGUGAUGAGAUAGAGCAC |
| SEQ ID NO. 18 | ACCAGGACAUCGUGCUCUA | UAGAGCACGAUGUCCUGGU |

FIGURE 2

| Modified NTARP siRNAs | Sense strand 5'-3' | Antisense strand 5'-3' | Chemical modifications |
|---|---|---|---|
| SEQ ID NO. 19 | cAc*cA*GGAcAucGuGcU*Cu | A*GAGCACCAUGUCCuGgug (SEQ ID NO. 20) | PS+2'OMe (S) / 2'OMe+PS (AS) |
| SEQ ID NO. 21 | cAc*cA*GGAcAucGuGcU*Cu | A*GAGCACGAUGUCCugGug (SEQ ID NO. 22) | PS+2'OMe (S) / 2'OMe+4'S+PS (AS) |
| SEQ ID NO. 23 | cAc*cA*GGAcAucGuGcU*Cu | A*GAGCACCAUGUCCpUGGpUG (SEQ ID NO. 24) | PS+2'OMe (S) / 5pU+PS (AS) |
| SEQ ID NO. 25 | cAc*cA*GGAcAucGuGcU*Cu | AGAGCACGAUGUCCuGGuG (SEQ ID NO. 26) | PS+2'OMe (S) / 2'O Me+2'F (AS) |
| SEQ ID NO. 27 | cAc*cA*GGAcAucGuGcU*Cu | AGAGCACGAUGUCCuGguG (SEQ ID NO. 28) | PS+2'OMe (S) / 2'OMe+2'F (AS) |
| SEQ ID NO. 29 | CAc*cA*GGAcAucGuGcU*Cu | AGAGCACGAUGUCCuGguG (SEQ ID NO. 30) | PS+2'OMe (S) / 2'OMe+2'F (AS) |
| SEQ ID NO. 31 | cAccAGGAcAcAucGuGcucu | AGAGCaCGAuGUCCuGguG (SEQ ID NO. 32) | 2'OMe (S) / 2'OMe+2'F (AS) |
| SEQ ID NO. 33 | CAccAGGAcAucGuGcucu | aGAGCaCGAuGUCCuGguG (SEQ ID NO. 34) | 2'OMe+2'F (S) / 2'OMe (AS) |
| SEQ ID NO. 35 | CACCAGGACACAUCGUGCUCUdTdT | AGAGCACGAUGUCCGGUGdTdT (SEQ ID NO. 36) | 2'H (S) / 2'H (AS) |
| SEQ ID NO. 37 | caCcAggaCaCaUcGuGcUcU | AGaGCaCGaUgUcCuGgUg (SEQ ID NO. 38) | 2'OMe+2'F (S) / 2'OMe+2'F (AS) |
| SEQ ID NO. 39 | cAccAGGAcAcAucGuGcucu | AGAGCACGAUGUCCUGGUG (SEQ ID NO. 40) | 2'OMe (S) / 2'OMe (AS) |
| SEQ ID NO. 41 | ACA*UC*GuGCUCuAuCUC*AU | AUGAGAUAGAGCACgAuGu (SEQ ID NO. 42) | PS+2'OMe (S) / 2'OMe (AS) |
| SEQ ID NO. 43 | AcA*UC*GuGCUCuAuCUc*AU | AUGAGAUAGAGCACAGgAuGu (SEQ ID NO. 44) | PS+2'OMe (S) / 2'OMe (AS) |
| SEQ ID NO. 45 | AcA*UC*GuGCUCuAuCUc*AU | AUGAGAUAGAGCACGApUGpU (SEQ ID NO. 46) | PS+2'OMe (S) / 5pU (AS) |
| SEQ ID NO. 47 | AcA*UC*GuGCUCuAuCUc*AU | A*UGAGAUAGAGCACGAuGu (SEQ ID NO. 48) | PS+2'OMe (S) / 4'S (AS) |
| SEQ ID NO. 49 | AcA*UC*GuGCUCuAuCUc*AU | AUGAGAUAGAGCACGAugu (SEQ ID NO. 50) | PS+2'OMe (S) / 4'S+2'OMe (AS) |
| SEQ ID NO. 51 | AcA*UC*GuGCUCuAuCUc*AU | AcGAGAUAGAGCACGAugu (SEQ ID NO. 52) | PS+2'OMe (S) / 4'S+2'OMe (AS) |
| SEQ ID NO. 53 | AcA*UC*GuGCUCuAuCUc*AU | A*UGAGAUAGAGCACGApUGpU (SEQ ID NO. 54) | PS+2'OMe (S) / 5pU(AS) |

FIG. 3A

| Modified NRARP siRNAs | Sense strand 5'-3' | Antisense strand 5'-3' | Chemical modifications |
|---|---|---|---|
| SEQ ID NO. 55 | AcA*uc*GuGCucuAucucA*U | A*UGAGAUAGAGCACGAuGu (SEQ ID NO. 56) | PS+2'OMe(S) / PS+5mU(AS) |
| SEQ ID NO. 57 | AcAucGuGcucuAucucAu | AuGAGAuAGAGCACGAuGu (SEQ ID NO. 58) | 2'F+2'OMe (S) / 2'OMe (AS) |
| SEQ ID NO. 59 | acAucGuGcucuAucucAu | AuGAGAuAGAGCACGAuGu (SEQ ID NO. 60) | 2'OMe (S) / 2'F+2'OMe (AS) |
| SEQ ID NO. 61 | ACAUCGUGCUCUAUCUCAUdTdT | AUGAGAUAGAGCACGAUGUdTdT (SEQ ID NO. 62) | dT(2'H) (S) / dT(2'H) (AS) |
| SEQ ID NO. 63 | AcAucGuGcucuAucucAu | AUGAGAuAGAGCACGAUGU (SEQ ID NO. 64) | 2'OMe (S) / 2'OMe (AS) |
| SEQ ID NO. 65 | acAuCgUgCuCuAuCuCaU | AUgAgAuAgAgCACgAuGu (SEQ ID NO. 66) | 2'OMe+2'F (S) / 2'OMe+2'F (AS) |

FIG. 3B

SIRNA AND THEIR USE IN METHODS AND COMPOSITIONS FOR INHIBITING THE EXPRESSION OF THE NRARP GENE

FIELD OF THE INVENTION

The present invention relates to the field of siRNA products and their use in methods and compositions for the treatment and/or prevention of retinal diseases related to neovascularization, and more particularly for the treatment and/or prevention of retinal diseases related to neovascularization related to high levels of expression and/or activity of NRARP gene.

BACKGROUND OF THE INVENTION

A healthy retina is necessary for good vision. Retinal disorders can cause partial or total loss of vision. Many retinal diseases share common symptoms and treatments, but each has unique characteristics. The goal of retinal disease treatments is to stop or slow disease progression and preserve or restore loss vision.

The neuroretina is a complex neurological tissue composed of a network of eight interconnected cell layers responsible for transforming visual light into electromechanical information that is sent to and interpreted by the brain through the optic nerve. The arrangement of the neural cells within the retina requires light to travel through most cell layers to reach the photoreceptors located in the posterior part of the retina; the photoreceptors thereafter transmit information to retinal neurons for local processing of visual information and transmission to the visual cortex. There are two types of photoreceptors, rods and cones. Both types of photoreceptors are present throughout the retina but rods dominate the periphery whereas cones are most dense in the center of the retina. The center of the retina, also known as macula, is a specialized region of the retina with densely packed cones and high concentration of pigments where vision is most acute. One of the main characteristics of the retina is its transparency. The transparency allows light to reach the outermost layer of the retina where the photoreceptors are located. This transparency requirement implies that the vasculature needed to nourish and support the retina is extremely specialized. Blood supply to the retina is provided by to main sources: the retinal vasculature and the choroid. The choroid is a highly vascularized, pigmented tissue lying between the retina and the sclera. The choroid provides nutrients, metabolites and gaseous exchange to the retina by diffusion through chorio-capillaries. The retinal pigment epithelium (RPE) is a monolayer of pigmented cells situated between the neuroretina and the choroid. RPE cells protect, support, and feed the light sensitive retina. The particular environment of the neuroretina is maintained by the blood-retinal barrier (BRB), also called hemato-retinal barrier. The BRB is constituted by the inner blood-retinal barrier and the external blood-retinal barrier. The inner blood-retinal barrier is formed by the tight junctions between capillary endothelial cells of the retinal vasculature. The external blood-retinal barrier is constituted by the tight junctions of RPE cells. Tight junctions between RPE cells are essential to control the transport of liquid and soluble compounds through the BRB, as well as to avoid entrance of toxic substances into the retina.

Blood vessels are formed in the retina by two major processes: vascularization or angiogenesis. Vascularization occurs as a result of differentiation of precursor cells, which are already present in the tissue, into the endothelial cells that contribute to the formation of blood vessels. Angiogenesis differs in that the new blood vessels are generated by sprouting from the preexisting vasculature. Angiogenesis requires proliferation, migration and differentiation of endothelial cells; as well as maturation of the newly formed vessels. The number of endothelial cells is normally stable in an adult organism; the stability in endothelia is controlled by a balance in the concentration of angiogenic and anti-angiogenic factors.

Alterations in the balance of factors lead to induction or suppression of angiogenesis. Vascularization and angiogenesis are natural processes that take place during development and other events such as healing; but these processes also have a role in the pathogenesis of certain diseases. Pathological neovascularization usually implies a combination of both vascularization and angiogenesis. There are two types of neovascularization that occur in the retina and both can cause vision loss: retinal neovascularization (RNV) in which new vessels sprout from the retinal capillaries and invade the vitreous and neural retinal layers, and choroidal neovascularization (CNV) in which new vessels sprout from the choroidal vasculature and invade the subretinal space. Although RNV and CNV originate from different vascular networks and invade different layers of the retina, shared molecular mechanisms promote the progression of both. RNV and CNV are the most common causes of severe visual loss in developed countries and new treatments are needed.

Vascular endothelial growth factor (VEGF), one of the most important mediators of angiogenesis, is upregulated during RNV and CNV. Over the last decade, scientists have developed several new "anti-VEGF" drugs. They help block abnormal blood vessels, slow their leakage, and help reduce vision loss. Treatment with anti-VEGF drugs is performed by intravitreal injections.

Intravitreal (IVT) injection is the most common method for delivering drugs to the back of the eye, which is used by all the currently approved drugs for the treatment of retinal disease with exception of verteporfin. Verteporfin is administered by intravenous injection followed by laser treatment, but its use has significantly decreased due to the marketing of the modern anti-VEGF treatments. The reasons behind the extended use of IVT injection are efficiency delivering drugs, level of familiarity to retinal physicians and ability of the physician to control treatment compliance (Rowe-Rendleman et al 2014). This method comes however with its own set of very specific disadvantages that include patient discomfort, risk of endophthalmitis, cataract formation and retinal detachment as well as high associated cost due to the office-based administration. Other methods of administration include periocular injection, suprachoroidal injection, sub-tenon injection and also eye drops. However, there is a certain scepticism about whether sufficient efficacy can be achieved to treat retinal conditions with eye drops, since the active ingredient has to be delivered from the cornea to its site of action in the retina. There are significant barriers and eliminations pathways that hinder the delivery of drugs to the back of the eye. Firstly only 1-7% of the administered drug is absorbed by the eye; most of the drug administered as eye drops is drained out of the eye or absorbed via the nasolacrimal duct to systemic circulation. In addition, drugs are rapidly cleared from the vitreous humor. There are two routes of clearance from the posterior cavity, the anterior and the posterior. The former entails clearance to the anterior chamber by the aqueous humor (AH) flow and thereafter by the AH outflow through the anterior chamber angle. The latter implies elimination through the blood-retinal barrier.

Thus, drugs that can easily permeate through the blood-retinal barrier would have a very short half-life in the vitreous humor.

An alternative to anti-VEGF drugs for the treatment of retinal diseases related to neovascularization are RNA interference (RNAi) based drugs.

RNAi is a naturally occurring post-transcriptional regulatory mechanism present in most eukaryotic cells that uses small double stranded RNA (dsRNA) molecules to direct homology-dependent gene silencing. Its discovery by Fire and Mello in the worm *C. elegans* {Fire et al 1998} was awarded the Nobel Prize in 2006. Shortly after its first description, RNAi was also shown to occur in mammalian cells by means of double-stranded small interfering RNAs (siRNAs) 21 nucleotides long {Elbashir et al 2001}.

The process of RNA interference is thought to be an evolutionarily-conserved cellular defence mechanism used to prevent the expression of foreign genes and is commonly shared by diverse phyla and flora, where it is called post-transcriptional gene silencing. Since the discovery of the RNAi mechanism there has been an explosion of research to uncover new compounds that can selectively alter gene expression as a new way to treat human disease by addressing targets that are otherwise "undruggable" with traditional pharmaceutical approaches involving small molecules or proteins.

According to current knowledge, the mechanism of RNAi is initiated when long double stranded RNAs are processed by an RNase III-like protein known as Dicer. The protein Dicer typically contains an N-terminal RNA helicase domain, an RNA-binding so-called Piwi/Argonaute/Zwille (PAZ) domain, two RNase III domains and a double-stranded RNA binding domain (dsRBD) {Collins et al 2005} and its activity leads to the processing of the long double stranded RNAs into 21-24 nucleotide double stranded siRNAs with 2 base 3' overhangs and a 5' phosphate and 3' hydroxyl group. The resulting siRNA duplexes are then incorporated into the effector complex known as RNA-induced silencing complex (RISC), where the antisense or guide strand of the siRNA guides RISC to recognize and cleave target mRNA sequences {Elbashir et al 2001} upon adenosine-triphosphate (ATP)-dependent unwinding of the double-stranded siRNA molecule through an RNA helicase activity {Nykanen et al 2001}. The catalytic activity of RISC, which leads to mRNA degradation, is mediated by the endonuclease Argonaute 2 (AGO2) {Liu et al 2004; Song et al 2004}. AGO2 belongs to the highly conserved Argonaute family of proteins. Argonaute proteins are ~100 KDa highly basic proteins that contain two common domains, namely PIWI and PAZ domains {Cerutti et al 2000}. The PIWI domain is crucial for the interaction with Dicer and contains the nuclease activity responsible for the cleavage of mRNAs. AGO2 uses one strand of the siRNA duplex as a guide to find messenger RNAs containing complementary sequences and cleaves the phosphodiester backbone between bases 10 and 11 relative to the guide strand's 5' end {Elbashir et al 2001}. An important step during the activation of RISC is the cleavage of the sense or passenger strand by AGO2, removing this strand from the complex {Rand et al 2005}. Crystallography studies analyzing the interaction between the siRNA guide strand and the PIWI domain reveal that it is only nucleotides 2 to 8 that constitute a "seed sequence" that directs target mRNA recognition by RISC, and that a mismatch of a single nucleotide in this sequence may drastically affect silencing capability of the molecule {Ma et al 2005; Doench et al 2004; Lewis et al 2003}. Once the mRNA has been cleaved, due to the presence of unprotected RNA ends in the fragments the mRNA is further cleaved and degraded by intracellular nucleases and will no longer be translated into proteins {Orban et al 2005} while RISC will be recycled for subsequent rounds {Hutvagner et al 2002}. This constitutes a catalytic process leading to the selective reduction of specific mRNA molecules and the corresponding proteins. It is possible to exploit this native mechanism for gene silencing with the purpose of regulating any gene(s) of choice by directly delivering siRNA effectors into the cells or tissues, where they will activate RISC and produce a potent and specific silencing of the targeted mRNA. RNAi has been applied in biomedical research such as treatment for HIV, viral hepatitis, cardiovascular and cerebrovascular diseases, metabolic disease, neurodegenerative disorders and cancer {Angaji S A et al 2010}.

Many studies have been published describing the ideal features a siRNA should have to achieve maximum effectiveness, regarding length, structure, chemical composition, and sequence. Initial parameters for siRNA design were set out by Tuschl and co-workers in WO02/44321, although many subsequent studies, algorithms and/or improvements have been published since then. siRNA selection approaches have become more sophisticated as mechanistic details have emerged, in addition further analysis of existing and new data can provide additional insights into further refinement of these approaches {Walton S P et al 2010}. Alternatively, several recent studies reported the design and analysis of novel RNAi-triggering structures distinct from the classical 19+2 siRNA structure and which do not conform to the key features of classical siRNA in terms of overhang, length, or symmetry, discussing the flexibility of the RNAi machinery in mammalian cells {Chang C I et al 2011}.

Also, a lot of effort has been put into enhancing siRNA stability as this is perceived as one of the main obstacles for therapy based on siRNA, given the ubiquitous nature of RNAses in biological fluids. Another inherent problem of siRNA molecules is their immunogenicity, whereby siRNAs have been found to induce unspecific activation of the innate immune system. The knockdown of unintended genes (mRNAs) is a well-known side effect of siRNA-mediated gene silencing. It is caused as a result of partial complementarity between the siRNA and mRNAs other than the intended target and causes off-target effects (OTEs) from genes having sequence complementarity to either siRNA strand. One of the main strategies followed for stability enhancement and OTE reduction has been the use of modified nucleotides such as 2'-O-methyl nucleotides, 2'-amino nucleotides, or nucleotides containing 2'-O or 4'-C methylene bridges. Also, the modification of the ribonucleotide backbone connecting adjacent nucleotides has been described, mainly by the introduction of phosphorothioate modified nucleotides. It seems that enhanced stability and/or reduction of immunogenicity are often inversely proportional to efficacy {Parrish, 2000}, and only a certain number, positions and/or combinations of modified nucleotides may result in a stable and non-immunogenic silencing compound. As this is an important hurdle for siRNA-based treatments, different studies have been published which describe certain modification patterns showing good results, examples of such include EP1527176, WO2008/050329, WO2008/104978 or WO2009/044392, although many more may be found in the literature {Sanghvi Y S. 2011; Deleavey et al 2012}.

The eye is a relatively isolated tissue compartment, which provides advantages for utilization of siRNA-based drugs for treating retinal diseases related to neovascularization. Feasibility of using siRNA for treatment of CNV has been demonstrated using siRNAs administered by intravitreal injection directed against VEGF or VEGF receptor 1 (VEGFR1) {Campochiaro P A. 2006}. Delivery of siRNAs by topical instillation to the posterior segment is truly challenging, because of the relatively large distance that the siRNAs have to go through the vitreous body before they reach the retina {Guzman-Aranguez A. et al 2013}. In addition, pharmaceutical treatment of retinal diseases affecting the posterior segment of the eye is also made challenging by restrictive blood ocular barriers such as the blood aqueous barrier (BAB) and the BRB, which separate the eye from systemic circulation. Furthermore, the compartmentalized structure of the eye limits the passage of siRNAs from the anterior chamber to the posterior segment of the eye {Duvvuri S et al 2003}. Finally, once siRNAs successfully enter the back of the eye, effective clearance mechanisms act to rapidly clear the delivered molecules {Del Amo E M et al 2008}. Thus, direct injection into the vitreous cavity has become the most efficient means to deliver siRNA-based therapeutics into the posterior segment of the eye {Edelhauser H F et al 2010}. Intravitreous injection of siRNAs achieves high concentrations of siRNAs that are locally available to the retinal tissues while limiting systemic exposure. However, the concentration of siRNAs is rapidly depleted from the posterior segment due to degradation by vitreous endonucleases and/or via permeation across the BRB and by diffusion across the vitreous to the anterior chamber. Thus, multiple intravitreal injections are required to maintain optimal siRNA concentrations within the posterior segment of the eye. The main disadvantage of this administration mode is that multiple intravitreal injections are associated with raised intraocular pressure, vitreous or retinal hemorrhage, retinal detachment, retinal tears, endophthalmitis, cataracts, floaters and transient blurry vision {Edelhauser H F et al 2010}. Therefore, while intravitreal injections ensure delivering a high concentration of siRNA to the retina, this method of administration also comes with its own set of particular risks. Consequently, topical administration of siRNAs could reduce risks and entail a more patient-friendly method of administration.

Naked siRNAs have shown to reach certain regions following topical applications, but access to deeper regions such as the innermost layer of the retina and effective cellular uptake require the development of strategies that ensure sufficient concentration of the compound reaching the cytoplasm of cells located in the target area and provoke a desired physiologic or therapeutic response. Physical approaches to deliver siRNAs across the stratum corneum barrier include microneedles (Chong, Gonzalez-Gonzalez et al., 2013), intradermal injection (Leachman, Hickerson et al., 2010), electroporation (Nakai, Kishida et al., 2007), iontophoresis (Kigasawa, Kajimoto et al., 2010) among others. Modifications of the molecule and/or formulation can also enable the molecule to penetrate into the required region and improve cellular uptake.

Topical administration of siRNA-based therapeutics for the treatment of retinal diseases has been described; for instance, US20130123330 discloses the treatment of diabetic retinopathy and other ocular neovascularization diseases by administering at least a siRNA duplex binding to mRNA molecules encoding VEGF or VEGFR2, or a cocktail combining siRNA duplexes targeting both genes VEGF and VEGFR2. This patent application described that the siRNA duplexes may be administered to the eye topically, subconjunctivally, or intravitreally. However, the specification only includes examples of compounds administered intravitreally or subconjunctivally. WO2010048352 (Quark Pharmaceuticals) discloses the use of chemically modified siRNA compounds for the treatment of ocular diseases, disorders and injuries associated with degeneration or death of retinal ganglion cells, including retinitis pigmentosa (RP), diabetic retinopathy (DR), diabetic macular edema (DME) and age related macular degeneration (AMD). Although the topical delivery to retinal tissue has been demonstrated for siRNA compounds which down-regulate the expression of target genes associated with loss of these cells, such as CASP2, RTP801, TIGASEII and p53 genes, only siRNA compounds targeting Caspase 2 have been proven to provide an ocular neuroprotective effect by increasing the survival of the retinal ganglion cells.

Target gene selection plays a key role when treating and/or preventing retinal diseases related to neovascularization with siRNA-based therapeutics. Notch-regulated ankyrin repeat protein (NRARP), is induced by Notch at newly formed branch points, where it differently modulates Notch and Wnt signaling activity to balance stalk proliferation and vessel stability. siRNA mediated downregulation of NRARP in HUVECs correlates with an increase in Notch, which in stalk cells is translated to vessel regression whereas increased Notch leads to formation of new tip-cells {Phng L K, Potente M, et al. 2009}. Therefore, it is likely that NRARP plays an important role in the regulation of the angiogenesis and/or neovascularization processes in retinal tissues.

siRNA-based therapeutics can slow down and prevent the progression of RNV and CNV in retinal diseases, but the therapeutic benefits can be diminished by inefficient siRNA delivery and the limited duration of siRNA bioavailability, which requires prolonged treatment regimens of repeated intravitreal injections. Thus, improved and non-invasive siRNA-based therapeutics targeting new and inventive target genes must be designed for the treatment and/or prevention of retinal diseases related to neovascularization.

SUMMARY OF THE INVENTION

The present invention provides improved products for reducing NRARP expression and consequently retinal diseases related to neovascularization. One of the advantages of treating retinal diseases related to neovascularization with siRNA products versus traditional anti-angiogenic therapeutic agents is that treatments based on siRNA will have a longer-lasting effect. This feature is due to the fact that siRNAs block the synthesis of the target protein. When treatment is suspended the cell will have to synthesise new target proteins from scratch; whereas traditional treatments would leave the target protein intact, ready to be active again once the inhibitor is no longer present. Another advantage could be increasing potency by using a combination of different siRNAs to treat the condition; this could be achieved by combining siRNAs targeting NRARP with other modulators of NRARP and/or other molecular mediators of neovascularization, such as VEGF or VEGFR2. The mechanism of action of siRNAs entails that once the active molecule reaches the cytoplasm the same molecule can be used to mediate the degradation of many mRNA molecules, this is not the case with antibodies, which require a 1:1 stoichiometry. Therefore it is anticipated that lower doses of the compounds will be needed to achieve the same clinical efficacy thus potentially reducing side effects.

DESCRIPTION OF THE DRAWINGS

FIG. 1: shows the short fragments of the target gene sequence of NRARP chosen as the target sequences for the siRNAs of the present invention.

FIG. 2: shows the oligonucleotide sequences for the siRNA molecules of the present invention targeting NRARP encompassed by the present invention. The SEQ ID NOs given in the Figure refer to the sense (5'→3') strand; typically siRNAs will be administered as dsRNAs, so siRNAs will include both the sense strand and its complementary antisense strand. SEQ ID NO. 10 to SEQ ID NO. 18 are siRNAs targeting SEQ ID NO. 1 to SEQ ID NO. 9 respectively. Generally, a siRNA will include the sense and antisense strand, and may also include 3' dinucleotide overhangs (for example, dTdT). However, this is not essential.

FIG. 3A and FIG. 3B: modified siRNAs targeting NRARP. SEQ ID NO 19 to SEQ; ID NO 40 refer to the modified sense (5'→3') strand and the modified antisense strand (5'→3') of siRNA SEQ ID NO 10, which targets sequence SEQ ID NO 1 of the NRARP gene. Legend: sense strand (S), antisense strand (AS), lower case (2'OMe ribonucleotides), *(PS or phosphothioate bond), lower case (4'Thioribose or 4'S), pU or 5 pU (5-Propynyluracile 3'), UPPER CASE (2'F ribonucleotides), lower case (5'-methyluridine or 5 mU), dT (deoxithymine o 2'H thymine).

DETAILED DESCRIPTION OF THE INVENTION

Figure 4:
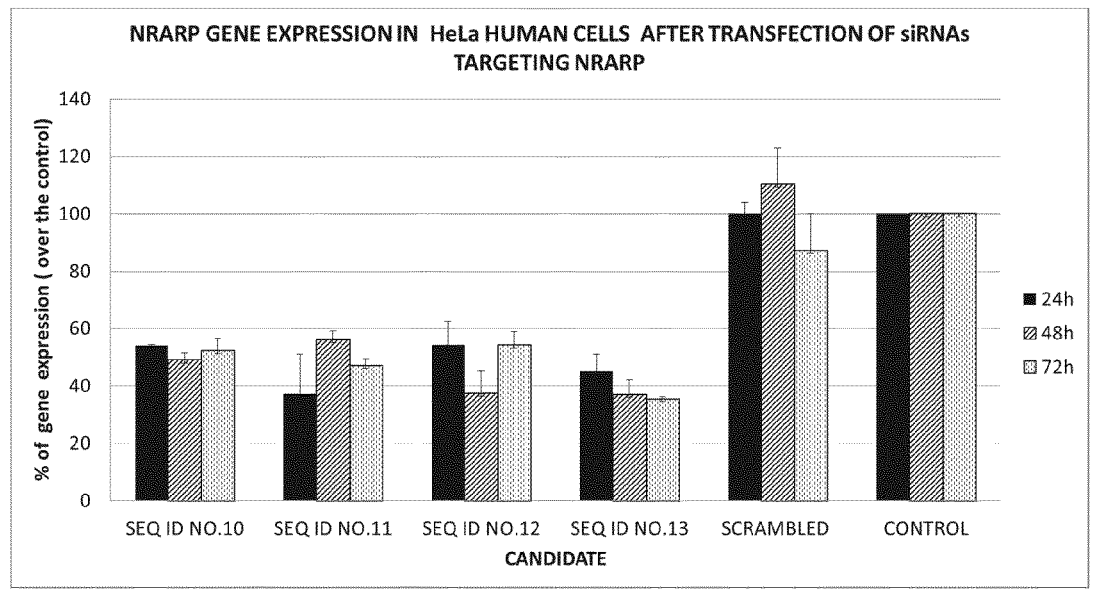
FIG. 4: in vitro NRARP gene expression levels after transfection of one of the following siRNAs targeting NRARP: SEQ ID NO. 10 (SYL136001), SEQ ID NO. 11 (SYL136005), SEQ ID NO. 12 (SYL136003) and SEQ ID NO. 13 (SYL136004) in human HeLa cells.

In a first aspect, the present invention relates to the provision of a siRNA molecule for use as a medicament, in the treatment and/or prevention of an eye condition characterised by increased expression and/or activity of NRARP, wherein said molecule specifically targets a sequence selected from the group consisting or comprising of: SEQ ID NO. 1 to SEQ ID NO. 9 and reduces expression of the NRARP gene when introduced in a cell. Preferably the target sequence comprises or consists of SEQ ID NO. 1.

A gene is "targeted" by a siRNA according to the present invention when, for example, the siRNA molecule selectively decreases or inhibits the expression of the gene. The phrase "selectively decrease or inhibit" as used herein encompasses siRNAs that affect expression of one gene, in this case NRARP. Alternatively, a siRNA targets a gene when (one strand of) the siRNA hybridizes under stringent conditions to the gene transcript, i.e. its mRNA. Hybridizing "under stringent conditions" means annealing to the target mRNA region under standard conditions, e.g., high temperature and/or low salt content which tend to disfavour hybridization. A suitable protocol (involving 0.1×SSC, 68° C. for 2 hours) is described in Maniatis, T., et al., Molecular Cloning: A Laboratory Manual, Cold Spring Harbor Laboratory, 1982, on pages 387-389.

Nucleic acid sequences cited herein are written in a 5' to 3' direction unless otherwise indicated. The term "nucleic acid" refers to either DNA or RNA or a modified form thereof comprising the purine or pyrimidine bases present in DNA (adenine "A", cytosine "C", guanine "G", thymine "T") or in RNA (adenine "A", cytosine "C", guanine "G", uracil "U"). Interfering RNAs provided herein may comprise "T" bases, for example at 3' ends, even though "T" bases do not naturally occur in RNA. In some cases these bases may appear as "dT" to differentiate deoxyribonucleotides present in a chain of ribonucleotides.

The target sequence as defined above is described as a target DNA sequence as used for definition of transcript variants in databases used for the purposes of designing siRNAs, whereas the specific compounds to be used will be RNA sequences defined as such.

An expert in the field can access any target gene sequence through public data bases. For example, the GenBank Accession Number corresponding to human NRARP mRNA is NP 001004354.1 and NM 001004354.2 (Gene ID: 441478). Furthermore, ENSEMBL (MBL-EBI/Wellcome Trust Sanger Institute) has the following NRARP human Accession Number: ENSG00000198435. All this information is in the free-access Ensembl data base.

Said preferred target region identified by the present invention comprises or consists of at least one sequence selected from SEQ ID NO. 1 to SEQ ID NO. 9.

In a preferred embodiment, said preferred target region comprises or consists of SEQ ID NO. 1.

These sequences present 100% homology between the following species: *Homo sapiens, Mus musculus, Rattus norvegicus, Canis lupus familiaris*, and *Sus scrofa domestica*.

In the RNAi field, when in vitro studies demonstrate that a human siRNA is not able to induce knock down of the animal model gene, a surrogate compound (animal-active analogue) is synthesized in order to analyze the efficacy of the siRNA in the relevant animal model. This surrogate is designed against the same region as the human siRNA, thus the two siRNAs have the same sequence except for a few nucleotides, depending on the homology between the human and the animal target gene. This approach has been widely used for development of other oligonucleotides, specifically for toxicology and efficacy studies {Kornbrust D et al 2013}.

In a more preferred embodiment, said preferred target region comprises or consists of SEQ ID NO. 1 (5'-CAC-CAGGACATCGTGCTCT-3').

Consequently, a siRNA according to the aspects of the present invention will preferably comprise a double stranded RNA molecule, whose antisense strand will comprise an RNA sequence substantially complementary to at least one sequence consisting of SEQ ID NO. 1 to SEQ ID NO. 9, and whose sense strand will comprise an RNA sequence complementary to the antisense strand, wherein both strands are hybridised by standard base pairing between nucleotides. More preferably, a siRNA according to aspects of the present invention will preferably comprise a double stranded RNA molecule, whose antisense strand will comprise an RNA sequence substantially complementary to SEQ ID NO. 1 to SEQ ID NO. 9, and even more preferably the antisense strand comprises or consists of an RNA sequence substantially complementary to SEQ ID NO. 1.

Within the meaning of the present invention "substantially complementary" to a target mRNA sequence, may also be understood as "substantially identical" to said target sequence. "Identity" as is known by one of ordinary skill in the art, is the degree of sequence relatedness between nucleotide sequences as determined by matching the order and identity of nucleotides between sequences. In one embodiment the antisense strand of an siRNA having 85%, 86%, 87%, 88%, 89%, 90%, 91%, 92%, 93%, 94%, 95%, 96%, 97%, 98% or 99% complementarity to the target mRNA sequence are considered substantially complementary and may be used in the present invention. The percentage of complementarity describes the percentage of contiguous nucleotides in a first nucleic acid molecule that can base pair in the Watson-Crick sense with a set of contiguous nucleotides in a second nucleic acid molecule. In a preferred embodiment, the antisense siRNA strand is 100% complementary to the target mRNA sequence, and the sense strand is 100% complementary to the antisense strand over the double stranded portion of the siRNA. The siRNA may also include unpaired overhangs, for example, 3' dinucleotide overhangs, preferably dTdT.

In a preferred embodiment, said eye condition (preferably a retinal eye condition) identified by the present invention is a disease or disorder related to neovascularization. More preferably, said eye condition is selected from age-related macular degeneration (AMD), ischemic retinopathy, diabetic macular edema (DME), proliferative diabetic retinopathy (PDR), diabetic retina ischemia (DRI), diabetic retinal edema (DRE), myopic neovascularization and retinopathy of prematurity (ROP) and combinations thereof.

As it is known from the state of the art, many different structures have been proposed to achieve RNA interference. Generally these double stranded molecules are from about 19 to about 25 nucleotides in length, and include blunt-ended structures as well as those with overhangs. Overhangs have been described to be advantageous and may be present on the 5' ends or on the 3' ends of either strand as they reduce recognition by RNAses and imitate Dicer's natural substrate. Some authors recommend including overhangs on both 3' ends of the molecules, whereas others consider one overhang to be sufficient. Others have described the use of blunt-ended structures with specific modification patterns (EP1527176, WO2005062937, WO2008104978, EP2322617, EP2348133, US20130130377, and many others).

Overhangs may be comprised of between 1 and 5 nucleotides; typically overhangs are made up of dinucleotides. Classical molecules used in the field, comprise a 19 nucleotide double stranded molecule which further comprises 3' dinucleotide overhangs preferably comprising deoxynucleotides as taught in initial studies by Tuschl (WO0244321).

These overhangs are said to further enhance resistance to nuclease (RNase) degradation. Later, Kim et al 2005 describe that 21-mer products (containing dinucleotide overhangs) are necessary for loading onto RISC. Further, Bramsen et al. 2009 describe the introduction of possible destabilizing modifications to the overhangs to further increase silencing efficiency.

As such, a preferred embodiment of the various aspects of the present invention refers to siRNA molecules targeting at least one sequence selected from the group consisting of SEQ ID NO. 1 to SEQ ID NO. 9 which comprise at least one overhang, preferably a 3' overhang in the sense and/or the antisense strand. More preferably, said siRNA molecules target SEQ ID NO. 1. Where the invention relates to a siRNA molecule targeting at least one sequence selected from SEQ ID NO. 1 to SEQ ID NO. 9, the siRNA will include an antisense strand of equivalent length and complementary to the target, and a sense strand of equivalent length and complementary to the antisense strand. The antisense and sense strands may further include additional bases which are not complementary to the other strand or the target, and/or which are not paired in the double stranded portion of the siRNA. For example, SEQ ID NO 1 is a 19 nucleotide sequence; the siRNA may include a 19 bp double stranded region over this portion of sequence identity, and additional dinucleotide overhangs.

A preferred embodiment of the various aspects of the present invention refers to siRNA molecules targeting at least one sequence selected from the group consisting of SEQ ID NO. 1 to SEQ ID NO. 9, wherein each strand of the double-stranded siRNA molecules is about 18 to about 28 or more (e.g., about 18, 19, 20, 21, 22, 23, 24, 25, 26, 27, or 28 or more) nucleotides long.

Another preferred embodiment of the various aspects of the present invention refers to siRNA molecules of 18-28 nucleotides long or more and comprising a nucleotide sequence selected from the group consisting of SEQ ID NO. 10 to SEQ ID NO. 18. More preferably, the double-stranded siRNA molecules are at least 19 nucleotides long and selected from the group consisting of SEQ ID NO. 10 to SEQ ID NO. 18.

Another alternative embodiment of the various aspects of the present invention provides blunt-ended molecules.

Further, a preferred embodiment of the present invention relates to a siRNA comprising or consisting of a 19 nucleotide double-stranded structure targeting at least one sequence selected from the group consisting of SEQ ID NO. 1 to SEQ ID NO. 9. More preferably, the siRNA comprising or consisting of a 19 nucleotide double-stranded structure targeting at least one sequence selected from the group consisting of SEQ ID NO. 1 to SEQ ID NO. 9, and even more preferably targeting SEQ ID NO. 1.

A particular embodiment of the present invention relates to a 19 nucleotide double-stranded blunt-ended siRNA targeted against at least one sequence selected from the group consisting of SEQ ID NO. 1 to SEQ ID NO. 9. More preferably, the siRNA is targeted against at least one sequence selected from the group consisting of SEQ ID NO. 1 to SEQ ID NO. 9, and even more preferably the siRNA is targeted against SEQ ID NO. 1. In a further particular embodiment this compound comprises or consists of at least one sequence selected from the group consisting of SEQ ID NO. 10 to SEQ ID NO. 18. In a further preferred embodiment, the antisense strand of this siRNA is at least 80%, preferably at least 90%, complementary to at least one sequence selected from the group consisting of SEQ ID NO. 1 to SEQ ID NO. 9.

In a preferred embodiment, this compound comprises or consists of at least one sequence selected from the group consisting of SEQ ID NO. 10 to SEQ ID NO. 18.

In another preferred embodiment, this compound comprises or consists of a sense strand which comprises or consists of at least one sequence selected from the group consisting of SEQ ID NO. 10 to SEQ ID NO. 18, and an antisense strand which is complementary to the sense strand.

In a more preferred embodiment, this compound comprises or consists of SEQ ID NO. 10 (5'-CACCAGGA-CAUCGUGCUCU-3' sense strand and 5'-AGAGCAC-GAUGUCCUGGUG-3' antisense strand), corresponding to our referenced compound named SYL136001.

Furthermore, as described in the section termed background of the invention, an important issue with siRNA molecules is their instability in biological fluids due to the ubiquitous nature of RNAses. Consequently, the use of many different chemical modifications to nucleotides has been described with the purpose of enhancing compound stability.

Another inherent problem of siRNA molecules is their immunogenicity, whereby siRNAs have been found to induce unspecific activation of the innate immune system, including up-regulation of certain cytokines, e.g. type I and/or type II interferon as well as IL-12, IL-6 and/or TNF-alpha production. The origin of these effects is thought to be activation of Toll-like receptors such as TLR7, TLR8 and/or TLR3 by siRNA.

Both of these effects, recognition by RNases and immunogenicity, have also been described to be sequence-dependent.

Some of the chemical modifications which enhance compound stability by decreasing susceptibility to RNAses are also able to reduce induction of immune recognition and consequently reduce the subsequent immune response. However, insertion of chemically modified nucleotides in a siRNA may also result in decreased silencing efficacy as described in the previous section, and hence must be approached with caution.

Consequently, in a preferred embodiment of the various aspects of the present invention, the siRNA further comprises at least one nucleotide with a chemical modification.

Preferred chemical modifications which enhance stability and reduce immunogenic effects include 2'-O-methyl nucleotides, 2'-fluoro nucleotides, 2'-amino nucleotides, 2'-deoxy nucleotides, or nucleotides containing 2'-O or 4'-C methylene bridges. Other preferred chemical modifications for exonuclease protection include the ExoEndoLight pattern of modification (EEL): modification of all pyrimidines in the sense strand to 2'-O-methyl residues, and modification of all pyrimidines in a 5'-UA-3' or 5'-CA-3' motif in the antisense strand to 2'-O-methyl residues. In addition, position 1 of the sense strand can also be changed to 2'-O-methyl to prevent 5'-phosphorylation of the sense strand and thus increasing strand-specificity of the siRNA. In addition, the sense strand can also include a 2'-O-methyl modification in position 14, because 2'-O-Me residues at this position inactivate the sense strand and therefore increase strand-specificity of the siRNAs. In addition, other preferred chemical modifications for nuclease protection include Methyl-Fluoro modification pattern (MEF): alternating 2'-fluoro and 2'-O-methyl modifications starting (5'-end) with a 2'-F on the sense strand and starting with 2'-O-Me on the antisense strand. In addition, position 1 of the sense strand can also be changed to 2'-O-Me and position 1 of the antisense strand to 2'-F (as 2'F residues are compatible with 5'-phosphorylation whereas 2'O—Me residues are bulky and generally impair phosphorylation). This modification pattern not only stabilizes the molecule but also disables the ability of the RISC to use the sense strand thus promoting strand-specificity. Also, modification of the ribonucleotide backbone can be performed by binding the nucleotides by using phosphorothioate bonds instead of phosphodiester links. A further preferred chemical modification within the meaning of the present invention relates to: 4'Thioribose, 5-Propynyluracile 3',5'-methyluridine or the substitution of uracyl ribonucleotides with deoxythymidine (deoxyribonucleotides). In another preferred embodiment of the present invention, the at least one chemically modified nucleotide and/or the at least one chemical modification in the ribonucleotide backbone is on the sense strand, on the antisense strand or on both strands of the siRNA.

Accordingly, in one embodiment, the siRNA comprises or consists of at least one sequence with a sense strand and/or an antisense strand selected from the group consisting of SEQ ID NO. 19 to SEQ ID NO. 66.

In a preferred embodiment, the siRNA comprises or consists of a sense strand which comprises or consists of at least one sequence selected from the group consisting of SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63 and SEQ ID NO. 65, and an antisense strand which is complementary to the sense strand which is selected from the group consisting of SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64 and SEQ ID NO. 66, respectively.

siRNA molecules as described above may be delivered to the cell interior in their native structure using methods known in the art. For example, when studying in vitro gene silencing, these compounds are administered using standard transfection reagents. To achieve effects in vivo these compounds may also be administered naked or using delivery enhancing agents such as for example liposomes, conjugation with a specific moiety, etc. although many different alternatives are known in the art, and are used differently depending on the desired target site within the body.

Alternatively, siRNA molecules of the various aspects of the invention can be expressed within cells from eukaryotic promoters. Recombinant vectors capable of expressing the siRNA molecules can be delivered and persist in target cells. Alternatively, vectors can be used that provide for transient expression of nucleic acid molecules. Such vectors can be repeatedly administered as necessary. Once expressed, the siRNA molecule interacts with the target mRNA and generates an RNA interfering response. The siRNA molecules produced in this manner are often termed shRNA (short hairpin RNA), as their sense and antisense strands are joined by a small loop of nucleotides. Delivery of siRNA molecules expressing vectors can be systemic, such as by intravenous or intra-muscular administration, by administration to target cells ex-planted from a subject followed by reintroduction into the subject, or by any other means that would allow for introduction into the desired target cell.

A further aspect of the invention relates to the use of siRNA targeting at least one sequence selected from the group consisting of SEQ ID NO. 1 to SEQ ID NO. 9 in the preparation of a medicament for use in a method of treatment of an eye condition characterised by increased expression and/or activity of NRARP. More preferably, said sequence is SEQ ID NO. 1. The method comprises inhibiting expression of NRARP in a patient. The term inhibition is used to indicate a decrease or downregulation of expression or activity. Preferably, the eye condition is a disease or disorder related to neovascularization. In one embodiment, the eye condition is selected from the group comprising age-related macular degeneration (AMD), ischemic retinopathy, diabetic macular edema (DME), proliferative diabetic retinopathy (PDR), diabetic retina ischemia (DRI), diabetic retinal edema (DRE), myopic choroidal neovascularization (also commonly being referred to as subretinal neovascularization, Fuchs' spot or Forster-Fuchs' retinal spot, and disciform degeneration in pathological myopia) and retinopathy of prematurity (ROP) and combinations thereof.

Also provided is a method of treatment of an eye condition characterised by increased expression and/or activity of NRARP. The method comprises inhibiting expression of NRARP in a patient. The method may comprise administering siRNA targeting at least one sequence selected from the group consisting of SEQ ID NO. 1 to SEQ ID NO. 9 More preferably, said sequence is SEQ ID NO. 1.

Therapeutic treatment with siRNAs directed against NRARP mRNA is expected to be beneficial over traditional anti-angiogenic therapeutic agents due to its specificity, stability, potency, natural mechanism of action, and uniform chemical nature with other siRNA agents targeting the same or different gene targets since they differ only in nucleotide sequence. Treatments based on siRNAs block the synthesis of the target protein which will provoke a sustained reduction of the NRARP gene expression and a longer-lasting effect that can avoid the consequences of an intravitreal injection. This is especially important in cases such as disease or disorder related to neovascularization, comprising but not limited to age-related macular degeneration (AMD), ischemic retinopathy, diabetic macular edema (DME), proliferative diabetic retinopathy (PDR), diabetic retina ischemia (DRI), diabetic retinal edema (DRE), myopic neovascularization and retinopathy of prematurity (ROP), as they are often chronic conditions which require numerous intravitreal injections during their treatment. Repetitive intraocular injections increase the risk of deleterious side effects which include, among others, increased pressure in the eye, inflammation, bleeding, infection, damage to the retina or surrounding nerves or structures, vision loss, but also side effects from the medicines that are used during the procedure, such as those derived from the use of antibiotics or drugs to dilate the pupils. Besides, siRNAs can be engineered to silence the expression of mutant gene alleles differing from wild type alleles by as little as a single nucleotide. Thus, treatments based on siRNA can advantageously modulate the expression of genes having point mutations to slow or even prevent disease, by inactivating disease mutant alleles selectively while allowing continued expression of the wild type protein.

Bearing in mind the preparation of such a medicament, the siRNA of the various aspects of the present invention may be formulated as a pharmaceutical composition. Preferably, the compositions and formulations of said siRNAs may be administered topically to the organ of interest. In an even more preferred embodiment they may be formulated for topical administration to the eye, preferably to the corneal surface of the eye. Application to the corneal surface may, for example be in the form of eye drops, a gel, lotion, cream or ocular inserts. Other administration forms to the eye may include injection into the eye.

A further preferred embodiment of the various aspects of the present invention relates to a siRNA specifically targeting at least one sequence selected from the group consisting of SEQ ID NO. 1 to SEQ ID NO. 9 as described in the preceding paragraphs, for use as a medicament for the treatment of an eye condition characterised by increased expression and/or activity of NRARP. More preferably, said sequence is SEQ ID NO. 1. As described above, it may be a siRNA comprising or consisting of a 19 nucleotide double-stranded structure targeting at least one sequence selected from the group consisting of SEQ ID NO. 1 to SEQ ID NO. 9. This siRNA may be blunt-ended. Preferably, the siRNA comprises or consists of at least one sequence selected from the group consisting of SEQ ID NO. 10 to SEQ ID NO. 18.

Other siRNA for use according to the invention comprises or consists of at least one sequence with a sense strand and/or an antisense strand selected from the group consisting of SEQ ID NO. 19 to SEQ ID NO. 66.

Within the context of the present invention, to "specifically target" a sequence the siRNA of the invention preferably comprises at least the same seed sequence. Thus, any sequence according to the invention that specifically targets at least one sequence selected from the group consisting of SEQ ID NO. 1 to SEQ ID NO. 9 is preferably identical in positions 2-8 of the antisense strand. More preferably, said selected sequence specifically targeted is SEQ ID NO. 1.

Notwithstanding the above, the siRNAs of the various aspects of the present invention may be used to silence NRARP expression in tissues other than the eye. Consequently, said siRNAs should be formulated accordingly.

For example, a siRNA molecule can comprise a delivery vehicle, including liposomes, for administration to a subject. Carriers and diluents and their salts can be present in pharmaceutically acceptable formulations. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins poly (lactic-co-glycolic) acid (PLGA) and PLCA microspheres, biodegradable nanocapsules, and bioadhesive microspheres, or by proteinaceous vectors. Intracellular delivery components can be also viral components which include, but are not limited to, a fusogenic viral peptide to disrupt endosomes, allowing the nucleic acid to avoid lysosomal degradation, viral proteins to maintain expression (e.g. integrase, LTR elements, rep proteins, oriP and EBNA-1 proteins) or viral components that interact with the cell surface proteins). Suitable viral intracellular delivery components include, but are not limited to, retroviruses, herpes simplex viruses, adenoviruses and preferably adeno-associated viruses (AAV). In one embodiment, the siRNA molecule is delivered through a cell-specific siRNA carrier that combines components of a virus and liposomes. In another embodiment, the nucleic acid molecules of the invention can also be formulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives. The preferred compositions of the invention are aqueous solutions, specifically saline solutions such as phosphate-buffered saline (PBS) with a pH range of about 7.0 to about 7.4, preferably with a pH of 7.2+0.5.

A siRNA molecule of the invention may be complexed with membrane disruptive agents and/or a cationic lipid or helper lipid molecule.

Delivery systems which may be used with the invention include, for example, aqueous and non-aqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer.

A pharmaceutical formulation of the invention is in a form suitable for administration, e.g., systemic or local administration, into a cell or subject, including for example a human. Suitable forms, in part, depend upon the use or the route of entry, for example oral, transdermal, or by injection. Other factors are known in the art, and include considerations such as toxicity and forms that prevent the composition or formulation from exerting its effect.

The present invention also includes compositions prepared for storage or administration that include a pharmaceutically effective amount of the desired compounds in a pharmaceutically acceptable carrier or diluent. Acceptable carriers or diluents for therapeutic use are well known in the pharmaceutical art. For example, preservatives, stabilizers, dyes and flavouring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) a disease state. The pharmaceutically effective dose generally depends on the type of disease, the composition used, the route of administration, the type of mammal being treated, the physical characteristics of the specific mammal under consideration, concurrent medication, and other factors that those skilled in the medical arts will recognize.

A therapeutically effective amount may also refer to the amount of a siRNA sufficient to delay or minimize the onset of an eye disorder associated with neovascularization preferably of the choroid or the retina. A therapeutically effective amount may also refer to the amount of the therapeutic agent that provides a therapeutic benefit in the treatment or management of an eye disorder associated with neovascularization preferably of the choroid or the retina. Further, a therapeutically effective amount with respect to a siRNA of the invention means that amount of therapeutic agent alone, or in combination with other therapies, that provides a therapeutic benefit in the treatment or management of an eye disorder associated with neovascularization preferably of the choroid or the retina. Used in connection with an amount of a siRNA of the invention, the term can encompass an amount that improves overall therapy, reduces or avoids unwanted effects, or enhances the therapeutic efficacy of or synergizes with another therapeutic agent.

A therapeutic benefit in the treatment or management of an eye disorder related to neovascularization is the sustained decrease in neovascularization. Given that siRNA will decrease the levels of NRARP within the cell, once the treatment stops the cell must re-synthesise new proteins. As such, therapies based on siRNA treatments will have a more sustained effect than those which might be expected using small molecules designed for inhibiting NRARP or blocking the function of the VEGF receptors or another protein associated to neovascularization. This is considered a significant enhancement of the therapeutic efficacy.

An additional benefit of using siRNA is the minimum probability of side effects or toxicity derived from its presence in systemic circulation, often associated with several eyedrop-based treatments. This is due to the fact that when the compound enters the bloodstream, it will be rapidly degraded by RNAses present in the blood.

On the other hand, the fact that the siRNA molecule can be marketed in single dose vials means addition of antimicrobial preservatives to the formulation can be avoided. These preservatives can produce intolerance in some patients, making it necessary to stop the treatment.

One of the preferred administration routes is topical, by instillation directly to the eye, preferably using eyedrops. Taking into account that the vast majority of the currently approved drugs for the treatment of retinal diseases are delivered by intravitreal injection, the quality of life of patients is also expected to be improved, since eye drops cause a minor discomfort and have fewer side effects than intravitreal injections.

However, as explained above, administration routes other than directly to the eye can also be used. The precise dosage and administration schedule to be employed in the formulation will also depend on the route of administration. A skilled person would understand that the precise dosage and administration schedule to be employed also depends on the seriousness of the disorder, and should be decided according to the judgment of the practitioner and each patient's circumstances. It is also understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

The formulations or siRNA of the invention and described herein can be administered in unit dosage formulations containing conventional non-toxic pharmaceutically acceptable carriers, adjuvants and/or vehicles. Formulations can be in a form suitable for oral use, for example, as tablets, troches, lozenges, aqueous or oily suspensions, dispersible powders or granules, emulsion, hard or soft capsules, or syrups or elixirs. Compositions intended for oral use can be prepared according to any method known to the art for the manufacture of pharmaceutical compositions and such compositions can contain one or more such sweetening agents, flavouring agents, colouring agents or preservative agents in order to provide pharmaceutically elegant and palatable preparations. Tablets contain the active ingredient in admixture with non-toxic pharmaceutically acceptable excipients that are suitable for the manufacture of tablets.

These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monostearate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in a mixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more colouring agents, one or more flavouring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavouring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavouring and colouring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavouring agents.

Syrups and elixirs can be formulated with sweetening agents, for example glycerol, propylene glycol, sorbitol, glucose or sucrose. Such formulations can also contain a demulcent, a preservative and flavouring and colouring agent. The pharmaceutical compositions or siRNA of the invention and described herein can be in the form of a sterile injectable aqueous or oleaginous suspension.

This suspension can be formulated according to the known art using those suitable dispersing or wetting agents and suspending agents that have been mentioned above.

A sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

In preferred embodiments, the compositions of the invention are formulated in a solution, preferably a buffered saline solution such as PBS, or a gel for topical administration to the eye, such as, for example, in the form of eyedrops. In such embodiments, the formulations may be cationic emulsions and/or contain biopolymers including, but not limited to, poly(lactide-co-glycolide), carbopol, hyaluronic acid and polyacrylic acid.

The nucleic acid molecules of the invention can also be administered in the form of suppositories, e. g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

As such, a further preferred embodiment of the present invention relates to a pharmaceutical composition wherein said composition comprises at least a siRNA targeting at least one sequence selected from the group consisting of SEQ ID NO. 1 to SEQ ID NO. 9, as has been described in the preceding paragraphs. More preferably, said sequence is SEQ ID NO. 1.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Following definitions are included in order to facilitate comprehension of the invention.

By "treat," the applicants mean to deal with medically. The term includes administering the compound of the invention to alleviate symptoms of a retinal disease, such as the decrease in visual acuity that accompanies macular degeneration, as well as to address the physiological changes associated with the disease, such as the abnormal blood vessel growth that accompanies that condition.

The term "retinal disease" means any disease in which the retina is affected due to multiple and variant etiologies.

The term "vascularization" refers to the process of formation of functional microvascular networks with red blood cell perfusion.

The term "angiogenesis" refers to the protrusion and outgrowth of capillary buds and sprouts from pre-existing blood vessels.

The term "retinal neovascularization (RNV)" refers to the sprout of new vessels in the retina.

The term "choroidal neovascularization (CNV)" refers to the sprout of new vessels from the choroidal vasculature.

The term "disease or disorder related to neovascularization" relates to any disease or disorder which generates the above-mentioned pathological new vessels. For such a disease or disorder, age-related macular degeneration (AMD), ischemic retinopathy, diabetic macular edema (DME), proliferative diabetic retinopathy (PDR), diabetic retina ischemia (DRI), diabetic retinal edema (DRE), myopic neovascularization, central retinal vein occlusion (CRVO) and retinopathy of prematurity (ROP), among others, can be mentioned but not limited thereto. Other ocular diseases or disorders related to neovascularization include, for instance, iris neovascularization (Rubeosis iridis) and corneal neovascularization (CN). Iris neovascularization is often associated with diabetes, retinoblastoma, central retinal vein occlusion, ocular ischemic syndrome or chronic retinal detachment. Corneal neovascularization is often caused by wearing contact lenses, although it is also associated to inflammation as the result of trauma or injury, and from blepharitis, uveitis, or keratitis, corneal ulcers, glaucoma and other ocular surface diseases like rosacea or lupus.

Macular degeneration, also referred to as age-related macular degeneration (AMD), is the most common cause of vision loss in the United States in those 50 or older, and its prevalence increases with age. The underlying cause for AMD seems to be accumulation of residual material produced by the renewal process of the external part of the photoreceptors of the retina in the retinal pigment epithelium (RPE). The accumulation of this undegraded material, known as drusen in the RPE leads to production of inflammatory mediators that cause photoreceptor degeneration in the central retina, or macula (Bird A C, 2010). The center of the macula, named fovea, mediates high acuity vision; hence its degeneration causes severe vision loss. In the early stages of the disease the accumulations of drusen are small and often observed along with hypo- or hyperpigmentation of the RPE. As the disease progresses both the size and the amount of drusen increase. AMD is classified as either wet (neovascular) or dry (non-neovascular). The dry form of the disease is most common. It occurs when the central retina has become distorted, pigmented, or most commonly, thinned, a process associated with atrophy of the retinal pigment epithelium and loss of macular photoreceptors. The result is central geographic atrophy. The wet form of the disease is more severe than the dry form and leads to severe vision loss. The wet form is usually associated with aging, but other diseases that can cause wet macular degeneration include severe myopia and some intraocular infections such as histoplasmosis, which may be exacerbated in individuals with AIDS. The wet form is characterized by abnormal blood vessels growing through the retinal pigment epithelium, resulting in hemorrhage, exudation, scarring, or retinal detachment.

Ischemic retinopathy is a common component of the pathogenesis of both CNV and RNV. Ischemia causes cellular hypoxia, which activates cellular signaling pathways to up-regulate the expression of angiogenic stimulators, such as vascular endothelial growth factor (VEGF). VEGF is a secreted glycoprotein with potent pro-angiogenic activity. VEGF binds to VEGF receptors (VEGFR) on endothelial cells to stimulate cell proliferation and migration. Numerous studies have shown that VEGF is up-regulated during the pathogenesis of CNV and RNV, and that VEGF is a key mediator of CNV and RNV pathogenesis.

Diabetic retinopathy (DR) remains the leading cause of blindness among working-age individuals in developed countries. Whereas proliferative diabetic retinopathy (PDR) is the commonest sight-threatening lesion in type 1 diabetes, diabetic macular edema (DME) is the primary cause of poor visual acuity in type 2 diabetes. Because of the high prevalence of type 2 diabetes, DME is the main cause of visual impairment in diabetic patients. In a large population-based study, the incidence of DME over a period of 10 years was 20% in patients with type 1 diabetes whereas this rate was almost 40% in patients with type 2 diabetes. In addition, DME is almost invariably present when PDR is detected in type 2 diabetic patients. Neovascularization due to severe hypoxia is the hallmark of PDR whereas vascular leakage due to the breakdown of the BRB is the main event involved in the pathogenesis of DME.

Retinopathy of prematurity (ROP) occurs in premature infants who are exposed to relative hyperoxia before the angiogenic phase of retinal development is complete. This is problematic, since the angiogenic phase of retinal development is normally driven by hypoxia in utero. Thus, normal angiogenic retinal development is disturbed in ROP, causing vaso-obliteration and the formation of a largely avascular retina. In the absence of an adequate blood supply, the avascular retina is ischemic, which promotes destructive RNV, and can lead to retinal detachment and the formation of scar tissue, resulting in permanent vision loss.

The term "patient," as used herein, refers to animals, including mammals, preferably humans.

The invention is further described in the following non-limiting examples.

EXAMPLES

1. In Vitro Analysis 1.1. Gene Expression Levels of NRARP After Transfection of SEQ ID NO. 10, SEQ ID NO.11 SEQ ID NO. 12 and SEQ ID NO. 13.

Human HeLa cells were transfected with 100 nM of one of 19 bp blunt ended dsRNA consisting of a sense strand consisting of one of the following sequences SEQ ID NO. 10 (SYL136001), SEQ ID NO. (SYL136005), SEQ ID NO. 12 (SYL136003), and SEQ ID NO. 13 (SYL136004), together with the complementary antisense strand, with Lipofectamine 2000 as transfecting agent. The SYL reference after each SEQ ID NO. refers to a reference for the dsRNA compound. Note that throughout these examples (unless the context makes otherwise clear), where administration or transfection of a particular SEQ ID NO is referred to, this indicates that 19 bp dsRNA was administered or transfected consisting of a sense strand consisting of the SEQ ID NO, and the complementary antisense strand as indicated in FIGS. 2 and 3. All transfections were performed following standard manufacturer's instructions. In the same experiment a scrambled siRNA sequence was used as control of the specificity of interference. Cell pellets were collected and processed to evaluate possible variations in mRNA levels as a consequence of siRNA mechanism of action. RNA levels were quantified by real-time PCR using a relative quantitation method, the comparative threshold $2^{-\Delta\Delta CT}$ method. {Livak and Schmittgen, 2001}. All real time quantitative PCR experiments were performed in triplicate and repeated in three independent experiments. Mean and SEM were calculated and are represented in the figures. As FIG. 4 shows, levels of NRARP mRNA decreased significantly (50-60%) in human HeLa cells in response to transfection of SEQ ID NO. 10, SEQ ID NO. 11, SEQ ID NO. 12, and SEQ ID NO. 13 at the three time-points studied. As expected, the scrambled siRNA sequence did not modulate NRARP expression levels at any of the time-points studied.

1.2 Cellular Viability of Human Cell Lines after Transfection with siRNAs of the Present Invention.

Figure 5:
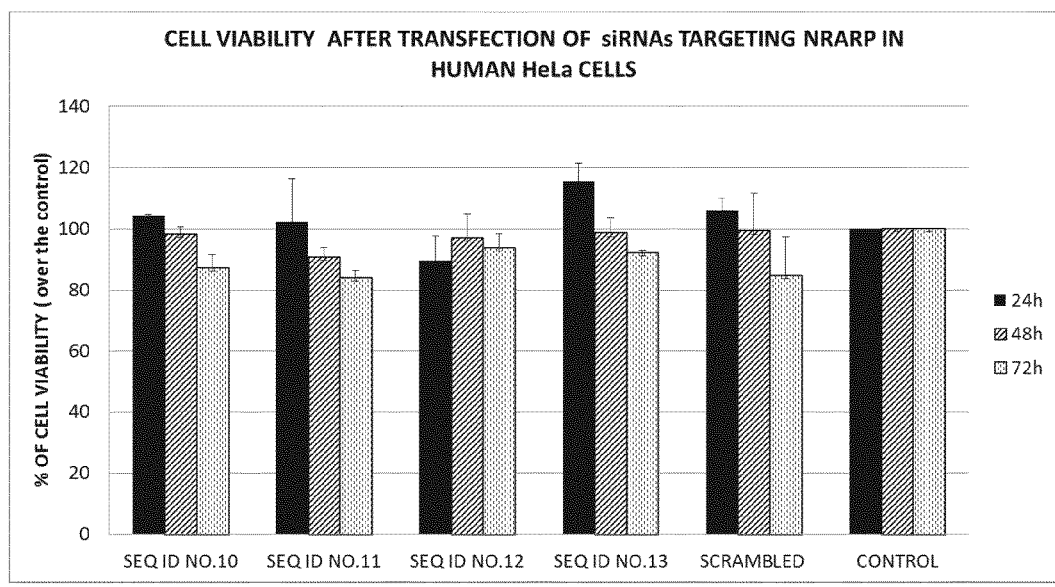
FIG. 5: in vitro cell viability after transfection of one of the following siRNAs targeting NRARP: SEQ ID NO. 10 (SYL136001), SEQ ID NO. 11 (SYL136005), SEQ ID NO. 12 (SYL136003) and SEQ ID NO. 13 (SYL136004) in human HeLa cells.

In order to analyze the cellular viability after transfection of the siRNAs of the present invention, in vitro toxicity was studied after transfection of 100 nM of one of the following sequences: SEQ ID NO. 10, SEQ ID NO. 11, SEQ ID NO. 12, and SEQ ID NO. 13, with Lipofectamine 2000 as transfecting agent in human HeLa cells. All transfections were performed following standard manufacturer's instructions. In the same experiment a scrambled siRNA sequence was used as a control of the specificity of interference. Cell pellets were collected at 24, 48, and 72 hours after transfection and processed to evaluate possible variations in cell viability. Cell viability was measured using CellTiter 96® Aqueous Non-Radiactive Cell Proliferation Assay from Promega. This method is based on capacity of living cells to reduce MTS tetrazolium into formazan. The amount of formazan is quantified by measuring the absorbance at 490 nm. Mean and SEM were calculated and plotted in FIG. 5. FIG. 5 shows that there were no changes in cell viability in response to transfection of any of the following sequences: SEQ ID NO. 10, SEQ ID NO. 11, SEQ ID NO. 12, and SEQ ID NO. 13. In summary, the siRNAs of the present invention were found to be non-toxic and are well tolerated.

1.3 NRARP Expression Levels After Transfection of Unmodified and Chemically Modified siRNA of the Present Invention in Different Cell Lines.

Figure 6:
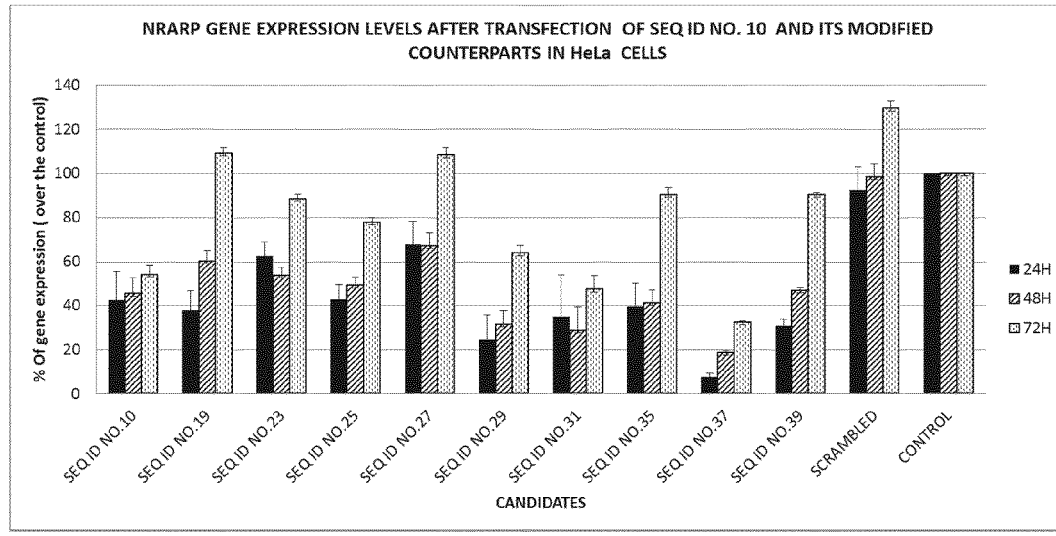
FIG. 6: in vitro NRARP gene expression levels after transfection of siRNA SEQ ID NO. 10 targeting NRARP and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in human HeLa cells.
Figure 7:
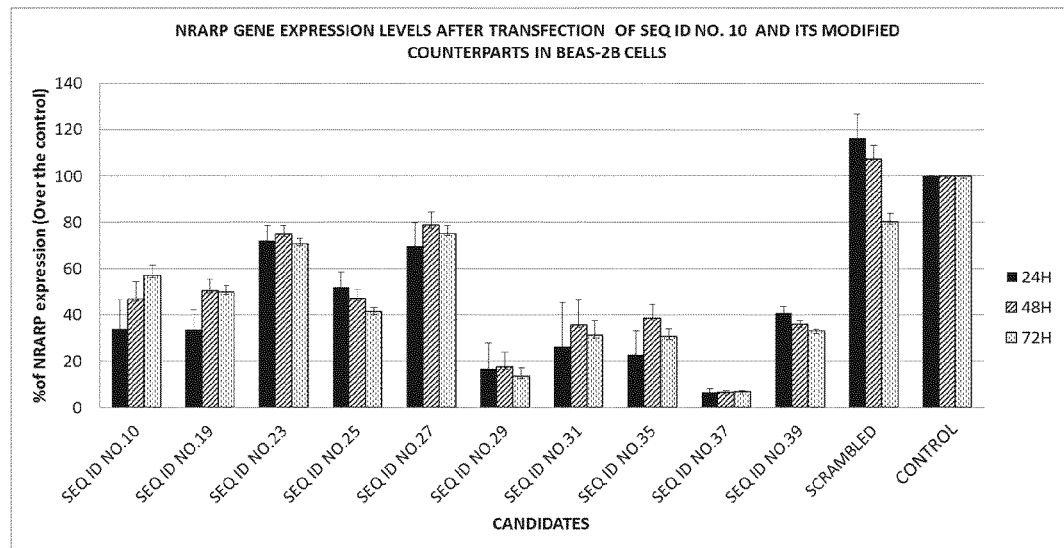
FIG. 7: in vitro NRARP gene expression levels after transfection of siRNA SEQ ID NO. 10 targeting NRARP and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in human BEAS-2B cells.
Figure 8:
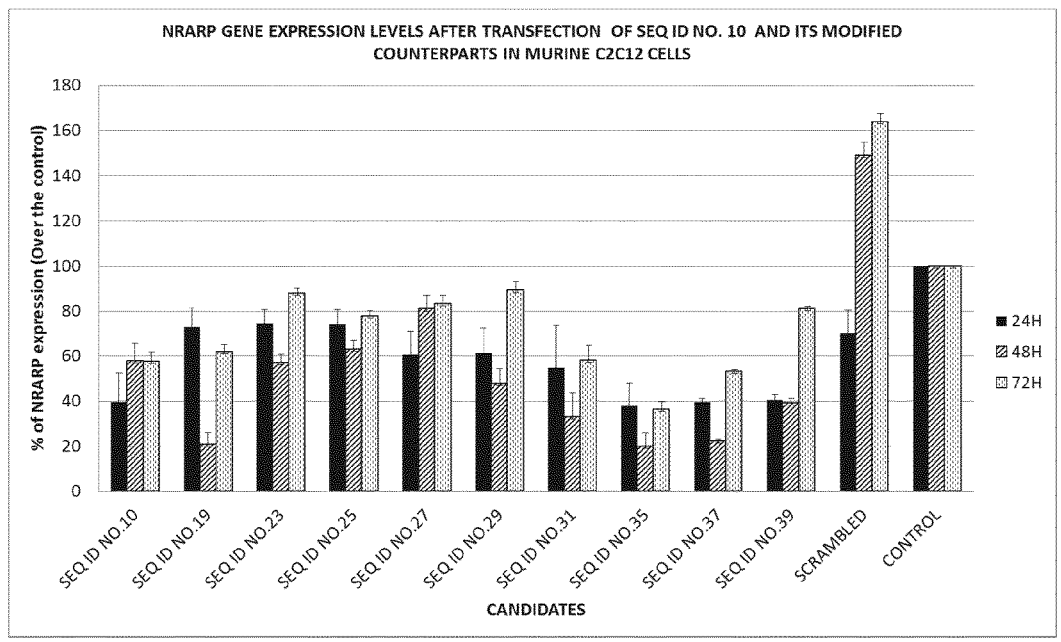
FIG. 8: in vitro NRARP gene expression levels after transfection of SEQ ID NO. 10 and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO, 39 in murine C2C12 cells.
Figure 9:
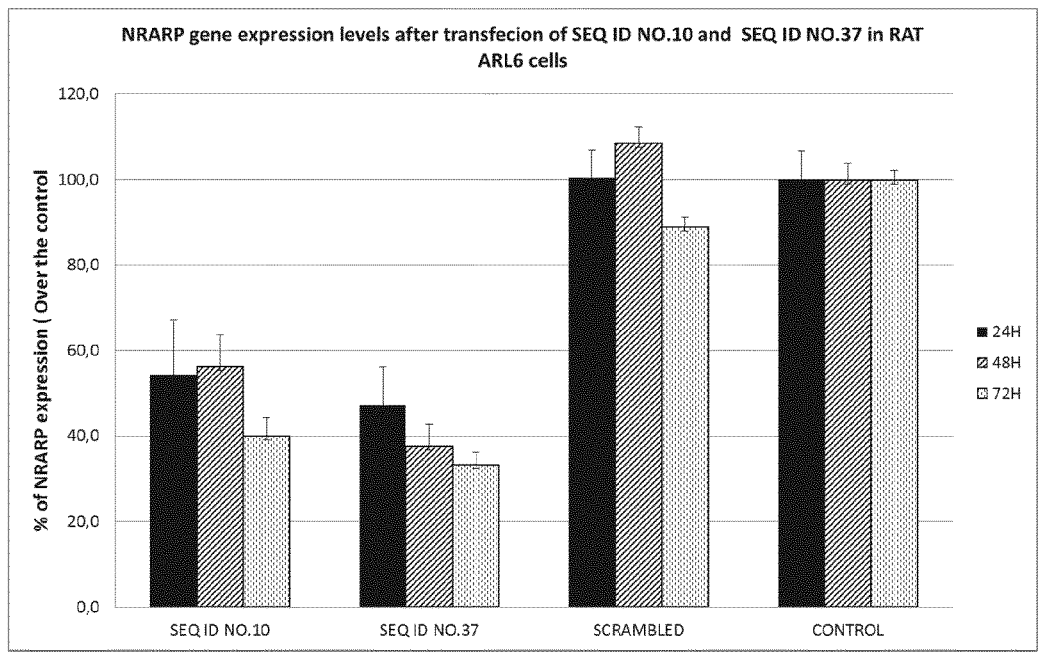
FIG. 9: in vitro NRARP gene expression levels after transfection of either SEQ ID NO. 10 or SEQ ID NO. 37 in RAT ARL6 cells.

In order to improve the stability of siRNAs of the present invention and to ensure no immunogenic activation, different siRNA-optimized chemical modifications were introduced to the canonical SEQ ID NO. 10 sequence (SYL136001); thus the following new chemically modified entities were obtained: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39. The new chemically modified sequences were individually transfected into human, murine and rat cells to analyze their ability of reducing NRARP mRNA levels. Chemical modifications are detailed in FIG. 3A and 3B. Human HeLa, human BEAS-2B and murine C2C12 cells were selected because these cells express significant levels of NRARP and are considered to be good models for studying the effect of siRNAs on NRARP expression. Cells were individually transfected with 100 nM of one of the following sequences: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39, with Lipofectamine (HeLa cells), Mirus Transit-X2 (BEAS-2B), Dharmarfect 3 (C2C12) and siPORT NeoFX (ARL6) as transfecting agents. Gene expression was analyzed at three time-points (24, 48 and 72 hours) following transfection. All transfections were performed following standard manufacturer's instructions. In the same experiment a scrambled siRNA sequence was used as control of the specificity of interference. RNA levels were quantified by real-time PCR using a relative quantitation method, the comparative threshold $2^{-\Delta\Delta CT}$ method {Livak and Schmittgen, 2001}. All real time quantitative PCR experiments were performed in triplicate and repeated in three independent experiments. Mean and SEM were calculated and plotted in the graphs shown in FIGS. 6-9. FIG. 6 shows the results obtained in HeLa cells. In this cell line SEQ ID NO. 10 (SYL136001) reduced NRARP mRNA levels 60% 24 hours after transfection and 50% 48 and 72 hours after transfection. The chemically modified SEQ ID NO. 19 reduced NRARP mRNA levels 60% 24 hours after transfection and 40% 48 hours after transfection; 72 hours after transfection basal levels were completely recovered. SEQ ID NO. 23 reduced NRARP mRNA levels 40% 24-48 hours after transfection and 10% 72 hours after transfection. SEQ ID NO. 25 reduced NRARP mRNA levels 50-60% 24-48 hours after transfection and 20% 72 hours after transfection. SEQ ID NO. 27 reduced NRARP mRNA levels 30% 24-48 hours after transfection and basal levels were recovered 72 hours after transfection. SEQ ID NO. 29 very effectively reduced NRARP mRNA levels. A reduction of approximately 80% was observed 24-48 hours after transfection in response to this sequence; thereafter mRNA levels increased but were still 40% below basal levels 72 h after transfection. SEQ ID NO. 31 effectively reduced NRARP levels, a 60% reduction vs. basal levels was observed at the three time-points studied. SEQ ID NO. 35 reduced NRARP mRNA levels 60% 24-48 hours after transfection; a sharp recovery of mRNA levels was found 72 hours after transfection, thus NRARP mRNA levels were 10% below basal levels. SEQ ID NO. 37 was the compound that caused the greatest reduction in the levels of NRARP mRNA. Reductions of and 70% were observed 24, 48 and 72 hours after transfection of this compound. SEQ ID NO. 39 reduced NRARP mRNA levels 70% 24 hours after transfection and 50% 48 h after transfection, thereafter mRNA levels sharply increased but basal levels were not completely recovered 72 hours after transfection. FIG. 7 shows the results obtained in human BEAS-2B cells. In this cell line, SEQ ID NO. 10 (SYL136001) and SEQ ID NO. 19 reduced NRARP levels 70% 24 hours after transfection, thereafter mRNA levels slowly increased but basal levels were not completely recovered within the time frame of the study with NRARP mRNA levels still 50% below basal levels 48 hours after transfection and 40%-50% 72 hours after transfection. SEQ ID NO. 23 and SEQ ID NO. 27 slightly reduced NRARP mRNA levels in human BEAS-2B cells, reductions were around 20-30% at the three time-points studied; basal levels were not completely recovered 72 hours after transfection. SEQ ID NO. 25 and SEQ ID NO. 39 gradually and time-dependently reduced NRARP mRNA levels reaching a maximal reduction of 50%-60% 72 hours after transfection. SEQ ID NO. 31 and SEQ ID NO. 35 effectively reduced NRARP mRNA levels; mRNA levels were approximately 60-70% below basal levels in response to either of the compounds at the three time-points studied. SEQ ID NO. 29 and SEQ ID NO. 37 were the most effective products reducing NRARP mRNA levels in this cell line, causing a sharply and sustained reduction of approximately 80% and 90% respectively at the three studied time points. As expected, the scrambled siRNA sequence did not reduce NRARP expression levels at any of the time-points studied. FIG. 8 shows the results obtained in murine C2C12 cells. SEQ ID NO. 10 (SYL136001) reduced NRARP levels 60% 24 hours after transfection, thereafter mRNA levels slowly increased but basal levels were not completely recovered 72 hours after transfection; time point at which NARP mRNA levels were still 40% below basal levels. SEQ ID NO. 19 reduced mRNA NRARP levels approximately 30% 24 hours after transfection, a dramatic reduction of 80% was found 48 hours after transfection, thereafter levels increased but 72 hours after transfection NARP mRNA levels were still 40% below basal levels. SEQ ID NO. 23, SEQ ID NO. 25 and SEQ ID NO. 27 slightly reduced mRNA NRARP levels, the reduction observed in response to transfection of each of these sequences was approximately 20-40% at the three time-points studied. SEQ ID NO. 29 and SEQ ID NO. 39 effectively reduced mRNA NRARP levels 24 and 48 hours after transfection, levels at these time-points were 50% and 60% below basal levels respectively. The response to both sequences 72 hours after transfection was an increase with respect to prior time-points although basal levels were still not recovered at this time-point. SEQ ID NO. 31 reduced mRNA NRARP levels approximately 40% 24 hours after transfection, a great reduction of 70% was found 48 hours after transfection, thereafter levels increased but 72 hours after transfection NRARP mRNA levels were still 40% below basal levels. SEQ ID NO. 35 and SEQ ID NO. 37, were the compounds that caused the greatest reduction in NRARP mRNA levels in this cell line, with SEQ ID NO. 35 and SEQ ID NO. 37 reducing NRARP mRNA levels, 60% 24 hours after transfection and approximately 80% 48 after transfection. A partial recovery of basal levels occurred 72 hours after transfection. Again, as expected, the scrambled siRNA sequence did not reduced NRARP mRNA levels at any of the time-points studied in C2C12 cells. FIG. 9 shows the results obtained in ARL6 rat cells. SEQ ID NO. 10 (SYL136001) reduced NRARP mRNA levels 50% 24-48 hours after transfection and 60% 72 hours after transfection. SEQ ID NO. 37 reduced NRARP levels 50% 24 hours after transfection, 60% 48 hours after transfection and 70% 72 hours after transfection.

1.4 Cellular Viability of Human Cell Lines after Transfection with Unmodified siRNAs and Chemically Modified siRNAs of the Present Invention in Different Cell Lines.

Figure 10:
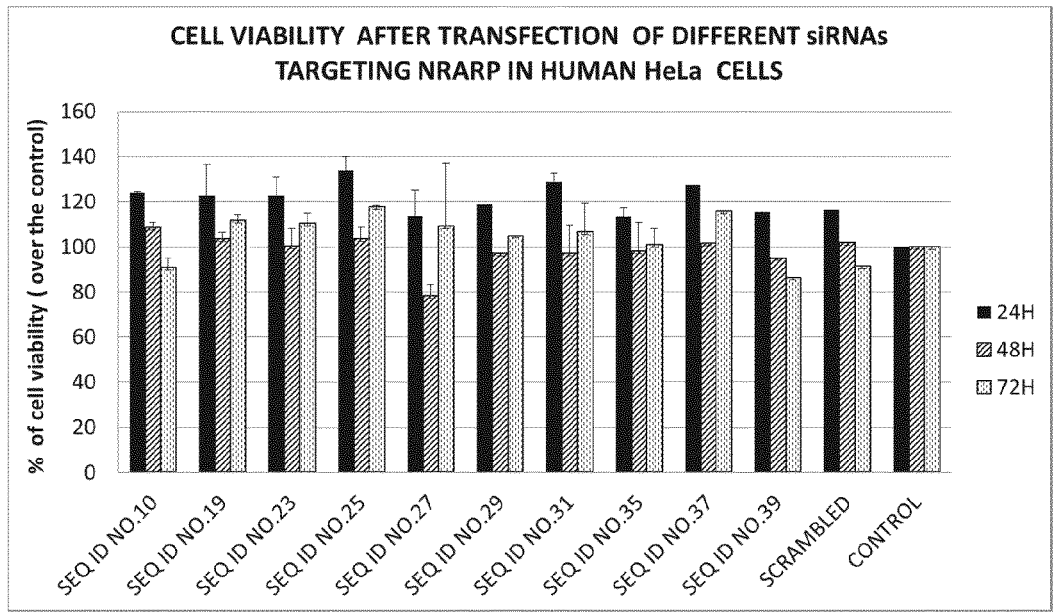
FIG. 10: in vitro cell viability after transfection of SEQ ID NO. 10 and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in human HeLa cells.
Figure 11:
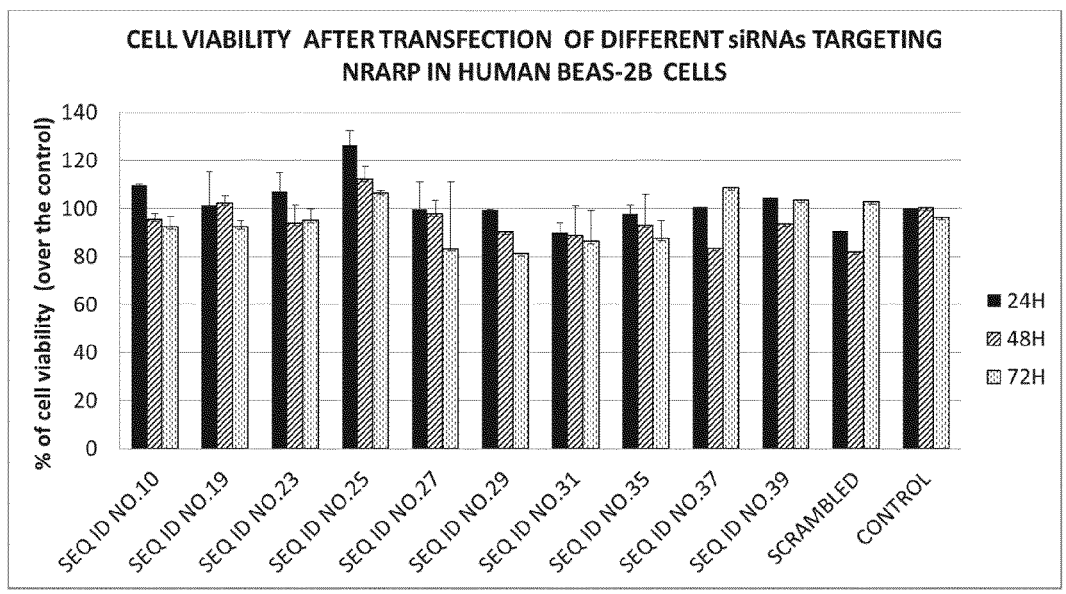
FIG. 11: in vitro cell viability after transfection of SEQ ID NO. 10 and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in human BEAS-2B cells.
Figure 12:
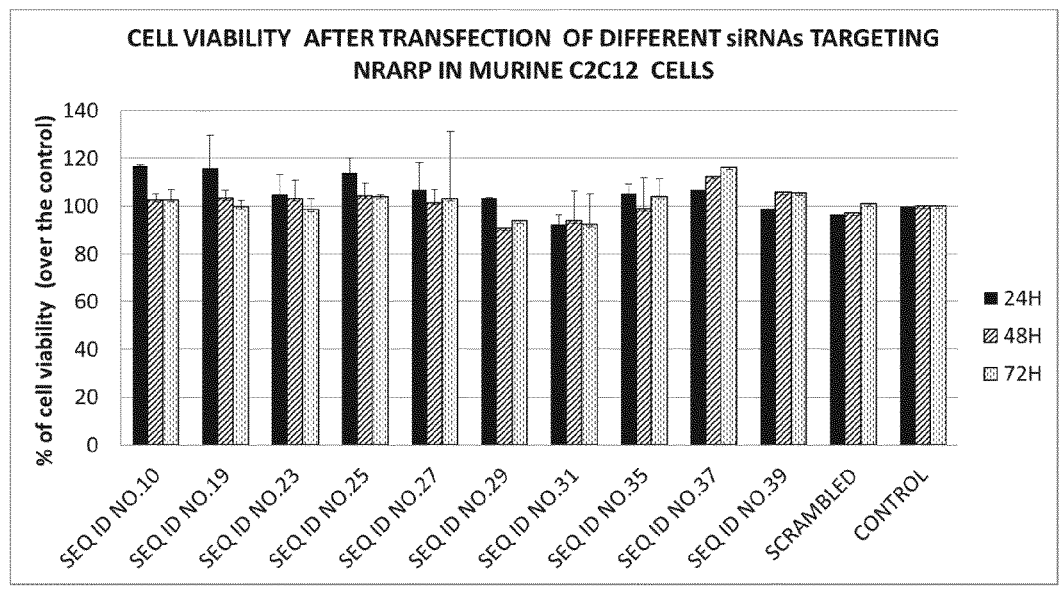
FIG. 12: in vitro cell viability after transfection of SEQ ID NO. 10 and its modified counterparts: SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in murine C2C12 cells.
Figure 13:
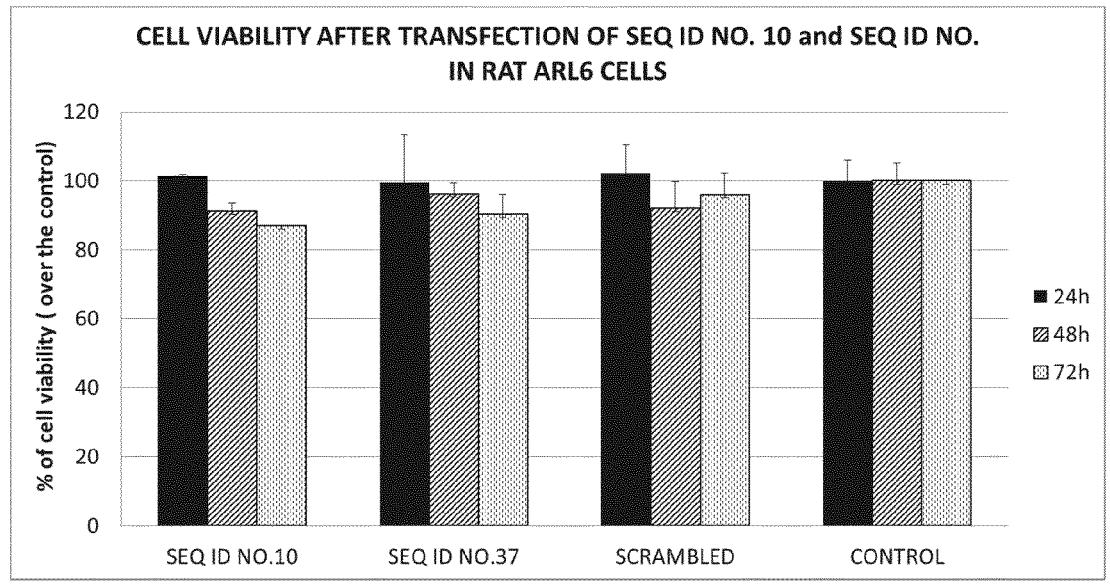
FIG. 13. in vitro cell viability after transfection of either SEQ ID NO. 10 or SEQ ID NO. 37 in rat ARL6 cells.

In order to analyze the cellular viability after transfection of the siRNAs of the present invention, in vitro toxicity studies were performed after transfection of 100 nM of one of the following sequences: SEQ ID NO. 10 (SYL13600), SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in human HeLa and BEAS-2B cells and in murine C2C12 cells with Lipofectamine 2000, Mirus Transit-X2, Dharmafect 3 as transfecting agents respectively. All transfections were performed following standard manufacturer's instructions. In the same experiments a scrambled siRNA sequence was used as a control of the specificity of interference. Cell pellets were collected at 24, 48, and 72 hours after transfection and processed to evaluate possible variations in cell viability as a consequence of siRNA transfection. Cell viability was measured using CellTiter 96® Aqueous Non-Radiactive Cell Proliferation Assay from Promega. This method is based on capacity of living cells to reduce the MTS tetrazolium compound into formazan which is measured by absorbance at 490 nm. Mean and SEM were calculated for each experiment and plotted in FIGS. 10-12. FIGS. 10, 11 and 12 show that there were no changes in cell viability in response to transfection of any of the following sequences: SEQ ID NO. 10 (SYL13600), SEQ ID NO. 19, SEQ ID NO. 23, SEQ ID NO. 25, SEQ ID NO. 27, SEQ ID NO. 29, SEQ ID NO. 31, SEQ ID NO. 35, SEQ ID NO. 37 and SEQ ID NO. 39 in any of the cell lines used. Furthermore, cell viability levels were also evaluated in ARL6 rat cells in response to transfection to one of the following sequences: SEQ ID NO. 10 (SYL136001) and SEQ ID NO. 37 using siPORT NeoFX as transfecting agent. FIG. 13 shows that there were no significant changes in cell viability in ARL6 cells in response to either of the tested sequences. We can therefore conclude that all the siRNAs of the present invention are non-toxic and well tolerated.

1.5 Efficacy of siRNAs of the Present Invention on Angiogenesis in an In Vitro Model of HUVEC Cells.

In order to study the effect of the siRNAs of the present invention on angiogenesis, experiments with HUVEC cells and analysis of the NRARP expression in these cells were performed.

In particular, the objective of these set of studies was to study the antiangiogenic effect of the modified NRARP siRNA SEQ ID NO. 37 (a 19 bp blunt ended dsRNA chemically modified having a sense strand consisting of sequence SEQ ID NO. 37 and a complementary antisense strand consisting of sequence SEQ ID NO. 38) in an in vitro model of HUVEC cells.

1.5.1 Introduction.

Angiogenesis is the formation of new veins from preexisting ones. This process, essential during development and several other physiological processes can be dysregulated in the eye leading to different types of retinal diseases, such as age-related macular degeneration (AMD) and diabetic retinopathy (DR). Human umbilical vein endothelial cells (HUVEC) are primary cells that have been preserved after 1-3 passages from the initial source material. These cells can be induced to form tubular structures in response to angiogenic agents such as VEGF.

1.5.2 Materials.

Multiscribe Reverse Transcriptase 50 U/ml (Applied Biosystems P/N 4311235).

RNAse inhibitor 20 U/µl (Applied Biosystems P/N N8080119). TaqMan 2× Universal Master Mix.

Qiagen" RNeasy Microkit 74004.

Human Nrarp probe: Taqman Gene Expression Assay Hs01104102_s1. GAPDH Endogenous control: Taqman Gene Expression Assay Hs00266705_g1.

Rat Nrarp probe: Taqman Gene Expression Assay Rn 03810258_s1 18S Endogenous control: Taqman Gene Expression Assay Hs99999901_s1.

1.5.3 Methods.

i) Cells

HUVEC cells (Ref: CC-2519/Batch number: 000191772) were obtained from Lonza. All experiments were performed with the same batch of cells at passage 6-9 and with cultures at a cell density of 75-85%. Transfections were performed using siPORT NeoFX™ following a standard procedure. For electroporation the procedure published in "Hernandez J L et al. 2004. Angiogenesis. 7:235-241" was followed, in briefly, 1×10$^6$ cells were electroporated by applying a 20 ms pulse at 1200 µF using the cell Manipulator® 600 (BTX). Each electroporation was performed using 2 µg of genetic material.

For the efficacy studies cells were transfected using the electroporation protocol and left to recover for a period of 24 h; thereafter cells were plated in 96-well plates at a density of 30.000 cells/well and the above mentioned parameters were analyzed 6 h after plating. Following structure analysis cells, media and matrigel were transferred into an RNase free tube and 600 µL of buffer RLT+ β-mercaptoethanol were added.

ii) Analysis of Target Gene Expression (1) RNA Isolation and Retrotranscription

Total RNA was isolated from cell cultures using RNeasy RNA extraction kit (Invitrogen, Calif., USA). 4 µg of total RNA were retrotranscribed using High-Capacity cDNA Archive kit (Applied Biosystems, Inc., Foster City, Calif., USA) according to the manufacturer's instructions.

(2) qPCR qPCR was performed using Stepone plus detection system (Applied Biosystems). 50 nanograms of each sample were amplified in a TaqMan 2× Universal Master Mix under the following conditions: 95° C. for 10 min, followed by 40 cycles of 95° C. for 15 s and 60° C. for 1 min.

1.5.4 Results.

Given the successful outcome of electroporation to introduce the siRNA into HUVEC cells this method was used for subsequent studies in which the role of the modified NRARP siRNA SEQ ID NO. 37 was assessed in the formation of capillary structures on matrigel, migration, wound healing and proliferation assays.

i) Formation of Capillary Structures.

(1) Set-Up of the Assay.

15.000 cells/well, deprived over a period of 4 h, were plated on a 96-well plate covered with matrigel. Endothelial cell basal medium (EBM) without supplements was used as negative control (no formation of structures) whereas complete medium with supplements (hEGF, hidrocortisone, bovine brain extract, gentamicine, heparine) and 10% FCS was used as a positive control inducing a maximal number of tubular structures. Assays were performed in triplicate in 3-6 independent experiments. Cultures were analysed 24 h after plating.

Figure 17:
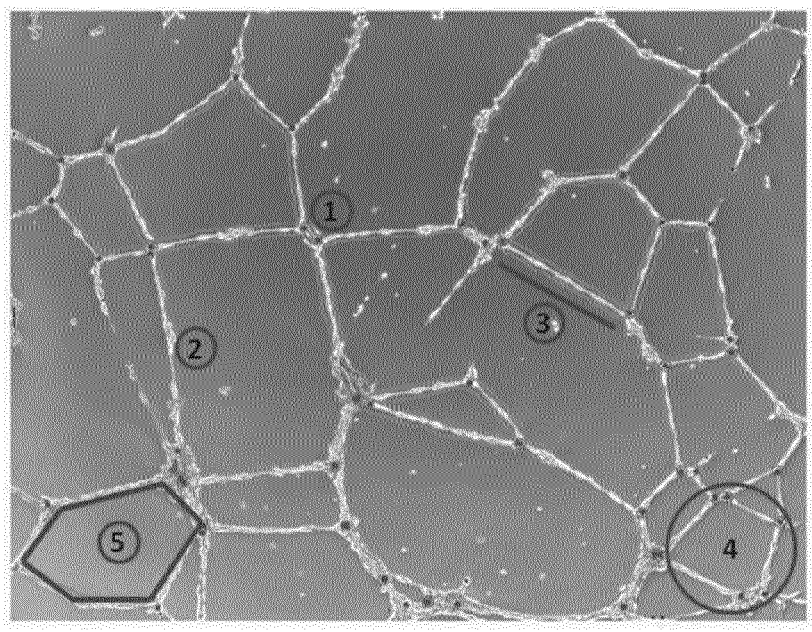
FIG. 17: Variables studied to assess the structures: 1.—Number of master junctions; 2.—Number of master segments; 3.—Total master segment length; 4.—Number of meshes; 5.—Total mesh area.

In addition, a new method for analysing the structures has been set up. This method is based on the quantification of 5 variables, using the Angiogenesis Analyzer software developed by Gilles Carpentier for NIH ImageJ. This software gives a global view over the angiogenic process. The variables studied are shown in FIG. 17.

Figure 18:
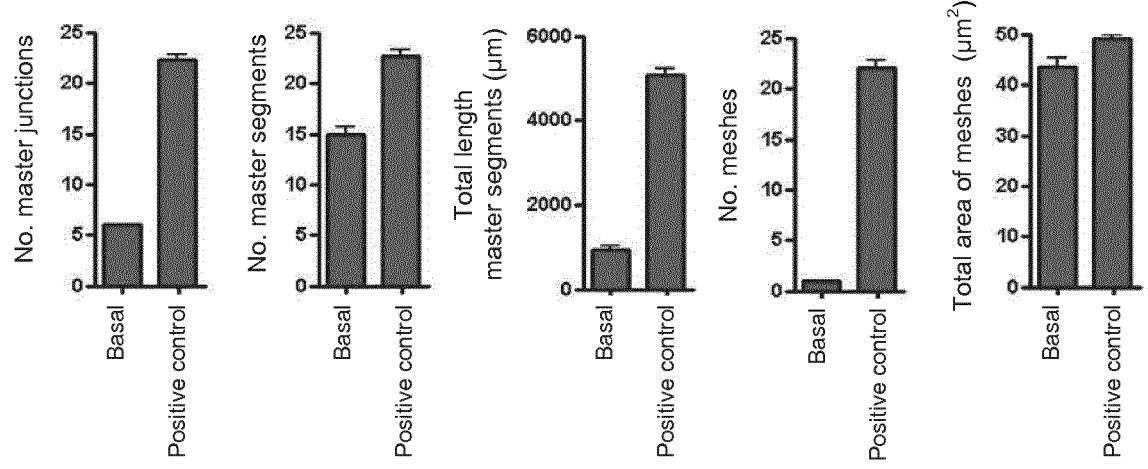
FIG. 18: Change in the different parameters studied in response to complete medium. The following parameters are represented: number of master junctions; number of master segments; total length of master segments; number of meshes; total area of meshes. Results were obtained from cells plated on culture dishes covered with matrigel using: EBM medium without supplements as negative control (basal), or complete medium with supplements and 10% FCS (positive control).

FIG. 18 shows the change in the variables studied in response to the complete medium (supplements +10% FCS). As shown in the figure the complete medium significantly increases the number of structures formed without altering the total area of the structures.

(2) Efficacy of siRNA SEQ ID NO. 37.

Cells were transfected by electroporation and allowed to recover in complete medium over a period of 24 h and deprived of serum for two additional hours; thereafter cells were plated at a cell density of 30.000 cells/well on a 96-well matrigel-covered plate to allow formation of structures. The structures formed were analyzed 6 h and 24 h after seeding. The following conditions were assayed to test the efficacy of SEQ ID NO. 37:

Non-transfected cells
Sham electroporated cells
Cells transfected with 1 µM siRNA anti-KDR (Life Technologies, Ref: 145034)
Cells transfected with 1 µM siRNA SEQ ID NO: 37.

All conditions were assayed in medium without supplements and with medium with 10% FCS and 100 ng/ml VEGF.

Figure 19:
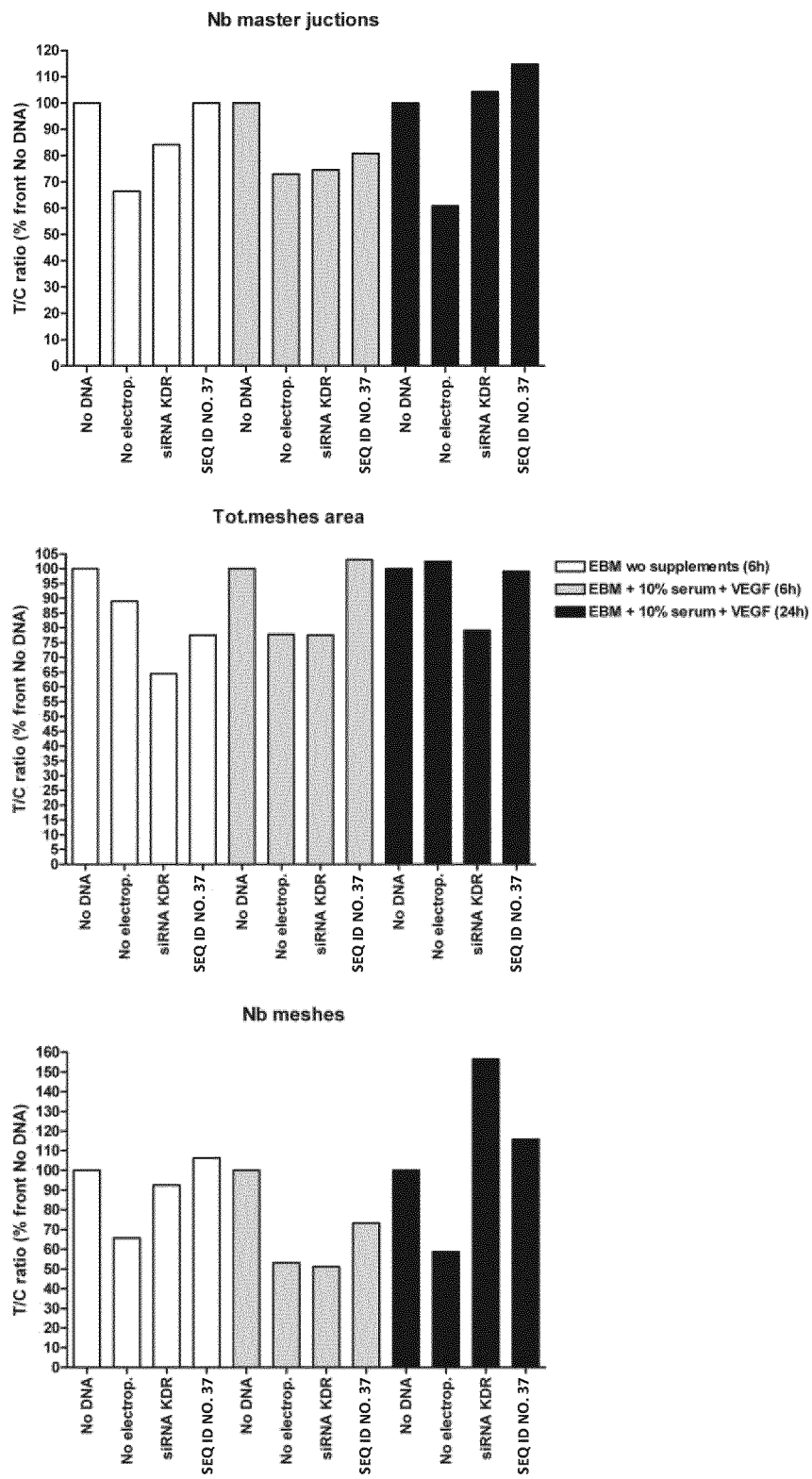
FIG. 19: Analysis of the different parameters studied in response to SEQ ID NO. 37 or KDR siRNA.
Figure 19:
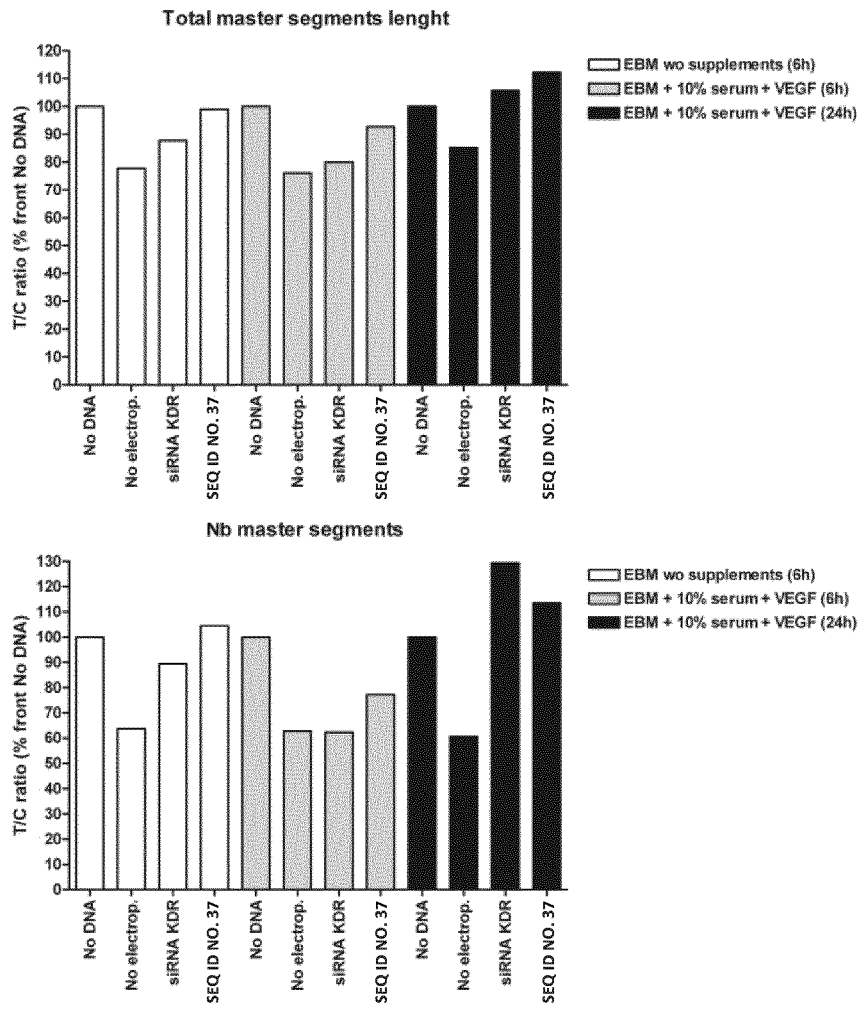
Figure 20:
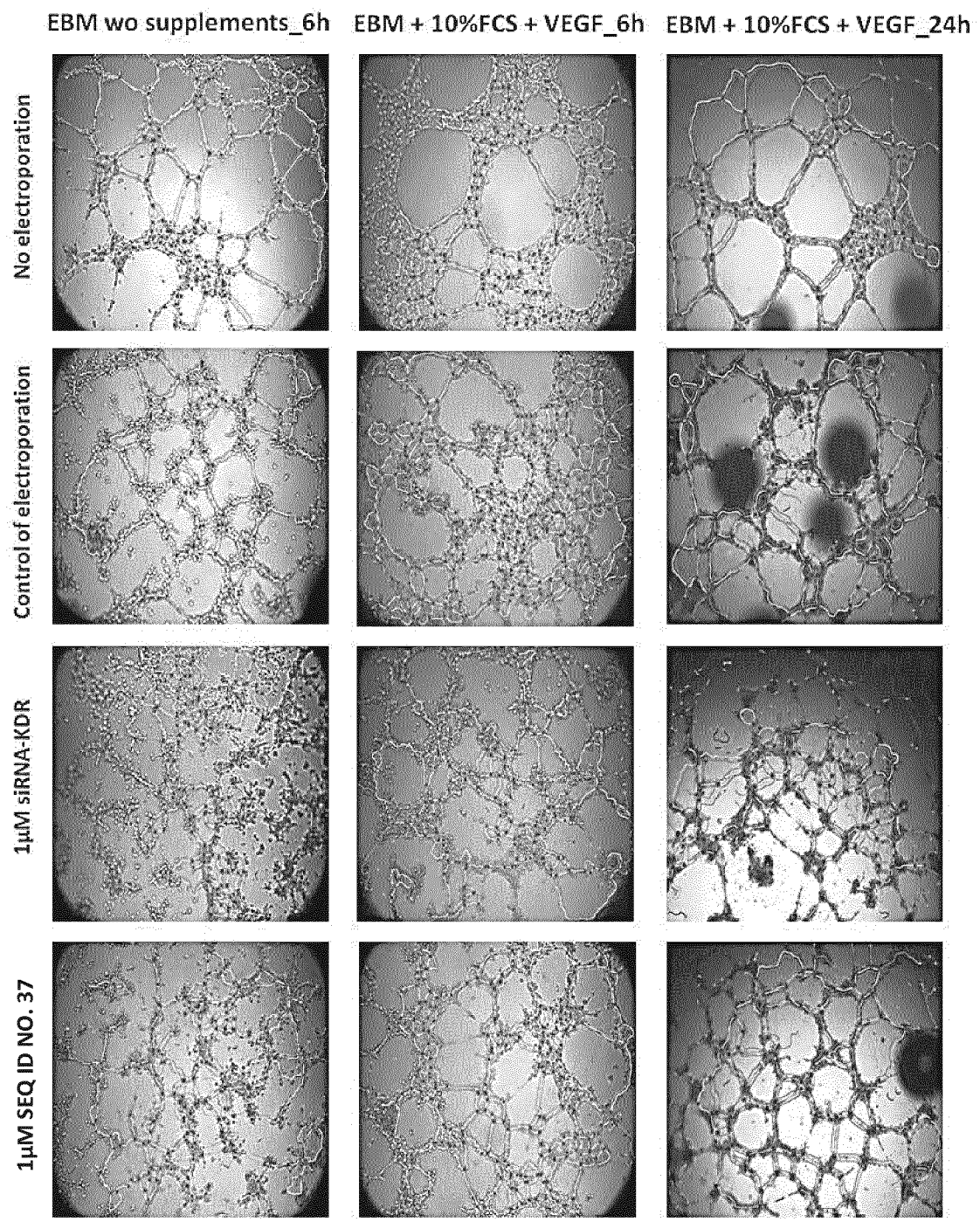
FIG. 20: Pictures of the structures formed in response to the different conditions.

A first assay was performed with cells that had been deprived in serum free medium for 2 h prior to seeding the cells on the matrigel. This procedure destabilized the structures slightly and was therefore repeated without the deprivation step. The results of the latter study are shown in FIGS. 19 and 20.

In summary, electroporation severely affects cell function; therefore comparisons were made between the sham electroporation condition and the experimental conditions. In absence of supplements, both the siRNA-KDR and siRNA-NRARP SEQ ID NO. 37 reduced the formation of angiogenic structures; the effect of siRNA-KDR was greater than that of siRNA SEQ ID NO. 37. The inhibitory effect of both siRNAs on the formation of angiogenic structures was clearer in the presence of complete medium with supplements at the 6 h time-point; this may be due to the fact that depriving the cells of serum and supplements may reduce cell viability. The analysis performed 24 h after seeding the cells on the matrigel was not conclusive because the structures had already started to disassemble.

ii) Effect on Proliferation.

(1) Set-up Assay.

Figure 21:
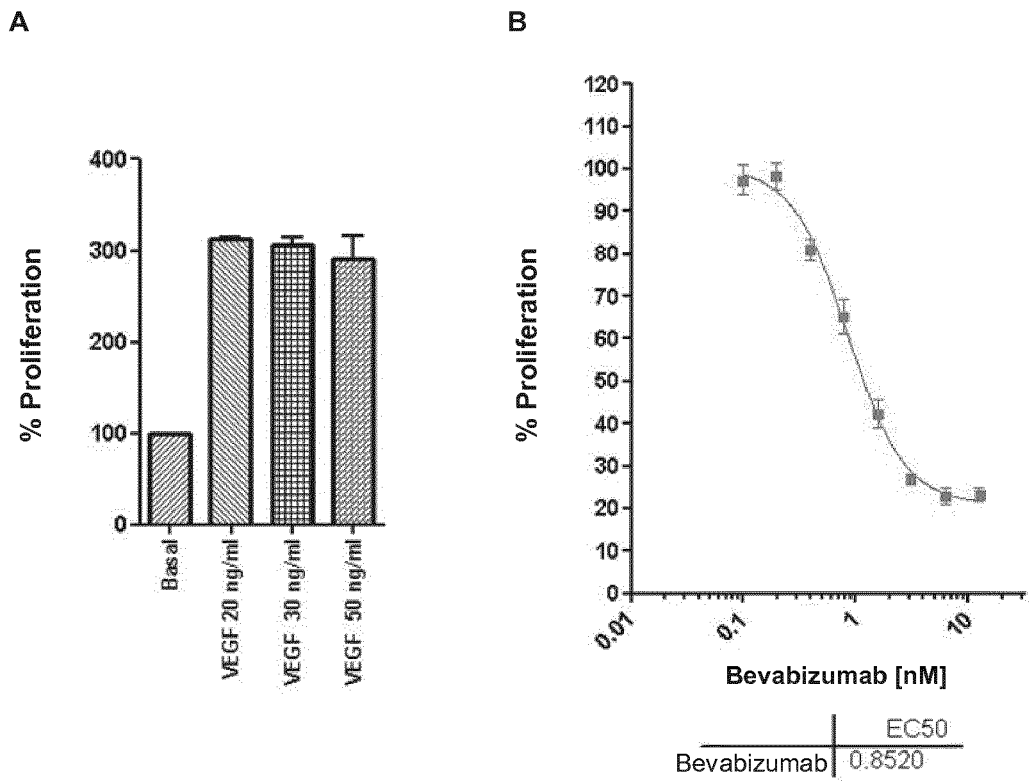
FIG. 21: A. Proliferation of HUVEC cells in response to different concentrations of VEGF. B. Inhibition of VEGF induced proliferation by bevabizumab.

24 h-deprived cells were plated in 96-well plates at a density of 3000 cells/well and cultured under the different conditions. Five days later proliferation was assessed by means of the MTT assay. The conditions used were as follows: 2% FCS and different concentrations of VEGF (20-30-50 ng/ml). 2% FCS is required for the cells keep a basal proliferation rate and avoid the culture entering into cell arrest. FIG. 21A shows a 3-fold induction in cell proliferation in response to VEGF, regardless of the concentration tested. In order to analyze the inhibitor effect of an anti-VEGF agent cells were cultured in presence of 30 ng/ml VEGF and decreasing concentrations (1:2 dilutions starting at 12 nM) of Bevabizumab (Avastin) in order to determine the IC50. As shown in FIG. 21B, the IC50 of bevacizumab was found to be 0.85 nM.

(2) Efficacy of siRNA SEQ ID NO. 37.

Cells were electroporated and plated at a density of 5000 cells/well in a 96-well plate coated with 1% gelatin; thereafter cells were allowed to recover for a period of 24 h. After recovery cells were and cultured in basal medium supplemented with 10% FCS and 100 ng/ml VEGF. Three days after plating the cells proliferation was analyzed by MTT. The conditions tested were as follows:
  Non-transfected cells
  Sham electroporated cells
  Cells transfected with 1 µM siRNA anti-KDR (Life Technologies, Ref: 145034)
  Cells transfected with 1 µM siRNA SEQ ID NO. 37.

Figure 22:
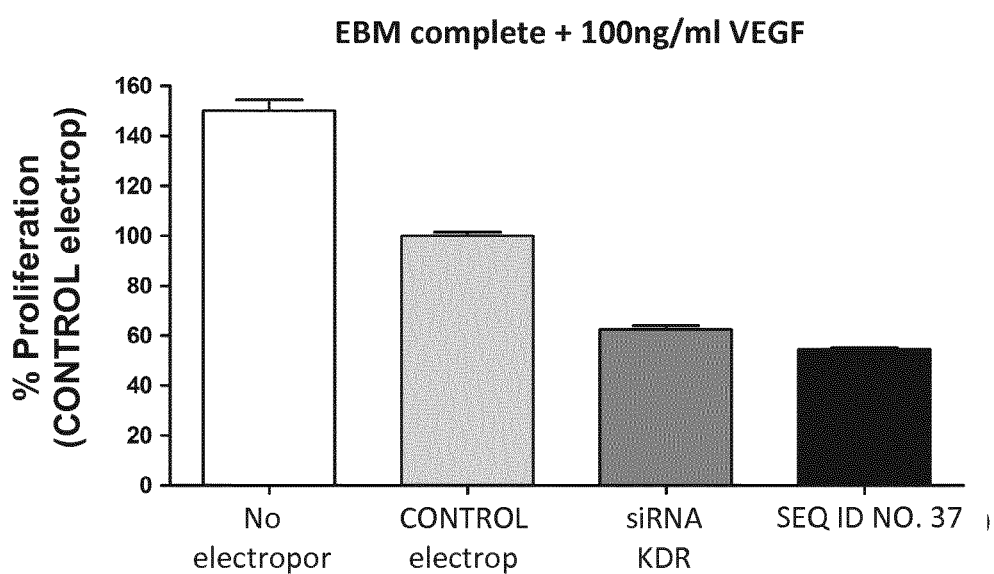
FIG. 22: Effect of anti-KDR siRNA or siRNA SEQ ID No. 37 on the proliferation induced by complete medium (10% FCS and 100 ng/ml VEGF) in HUVEC cells.

The results, shown in FIG. 22, indicate that both the siRNA anti-KDR and siRNA SEQ ID No. 37 reduce the rate of proliferation induced by VEGF in approximately 40% compared to the sham electroporated cells.

iii) Effect on Migration.

(1) Set-up Assay.

These studies were performed in 24-transwell system plates with 8 µm opaque membrane filters (Transwell HTS FluroBlok™ Multiwell Insert System de Becton Dickinson). Both surfaces of the membrane were covered with type I collagen at a concentration of 15 µg/ml during 2 h at 37° C. to facilitate cellular absorption. Cells were plated at a density of 50.000 cells/well and serum deprived over a period of 4 h and thereafter the migration stimulus was added. 24 h after adding the stimulus on the inferior part of the transwell the number of cells that had migrated to the superior compartment was analyzed following staining with Calcein-AM.

The number of migrating cells in complete medium (10% FCS and supplements) was used as a positive control of cell migration and this response was compared to the one produced by increasing concentration of VEGF (1-10-100 ng/ml).

Figure 23:
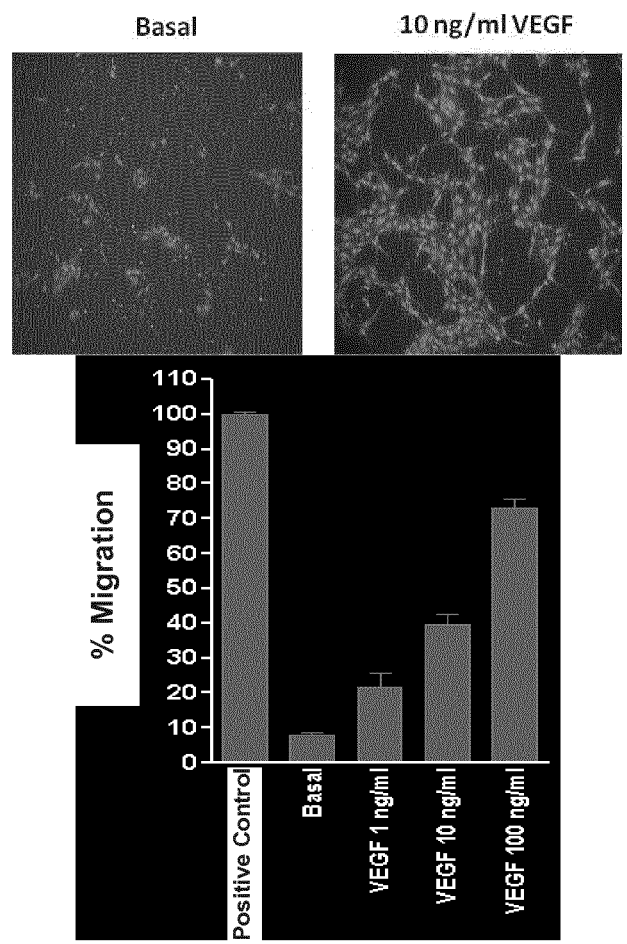
FIG. 23: Migration of HUVEC cells in response to increasing doses of VEGF.

As show on FIG. 23, VEGF induces a dose dependent increase in the number of cells migrating to the superior compartment. The maximal increase in response to VEGF was observed in response to the greatest concentration of VEGF (100 ng/ml) and the magnitude of the response was around 5-6 fold over basal conditions.

(2) Efficacy of siRNA SEQ ID NO. 37.

Cells were electroporated and allowed to recover for a period of 24 h; thereafter cells were plated at a density of 10.000 cells/well on 96-transwell plates with 8 µm opaque membrane filters coated with 15 µg/ml collagen. All the conditions tested were assayed in the presence of basal medium and complete medium (supplemented with 10% FCS and 100 ng/ml VEGF). The conditions tested were as follows and migration was analyzed 24 h after plating and staining the cells with calcein-AM:
  Non-transfected cells
  Sham electroporated cells
  Cells transfected with 1 µM siRNA anti-KDR (Life Technologies, Ref: 145034)
  Cells transfected with 1 µM siRNA SEQ ID NO. 37.

Figure 24:
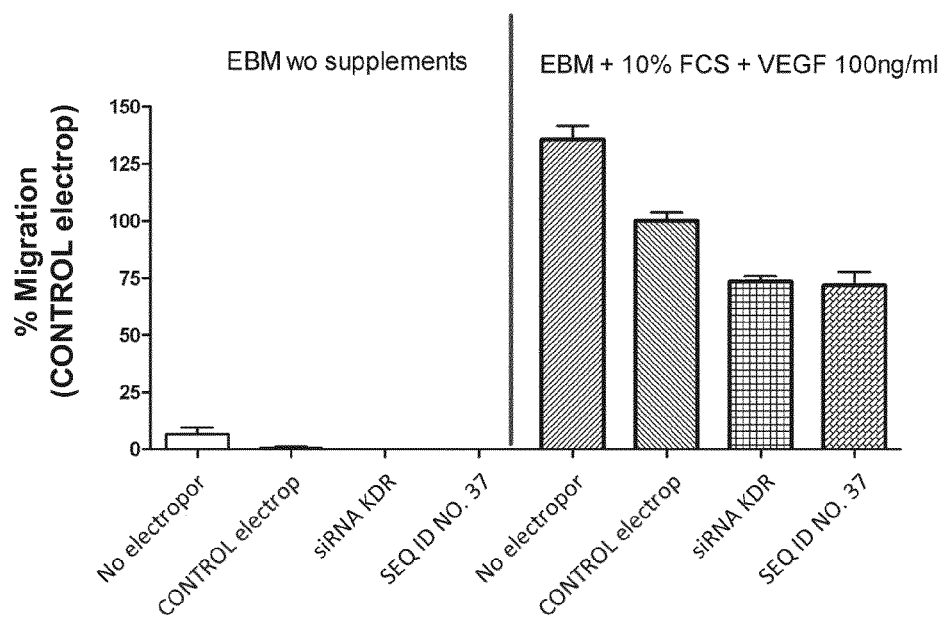
FIG. 24: Effect of anti-KDR siRNA or siRNA SEQ ID NO. 37 on the migration of HUVEC cells induced by medium without supplements and complete medium (10% FCS+100 ng/ml VEGF).
Figure 25:
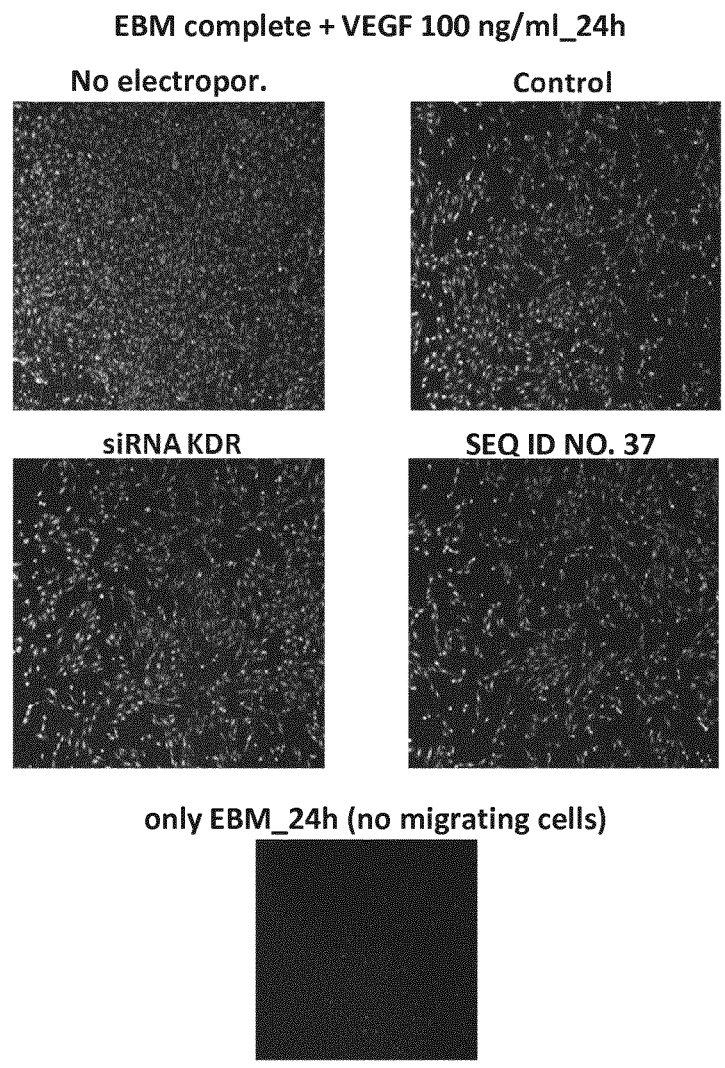
FIG. 25: Pictures of cells in the upper compartment (migrating) in response to the different conditions.

The results obtained indicate that electroporation had a deleterious effect on the migration capacity of cells; therefore treated cells were compared to the sham electroporated condition in order discard the effect of electroporation. Cells in basal medium did not migrate but the presence of 10% FCS and 100 ng/ml VEGF caused cells to migrate to the opposite well in the transwell system. The effect of 10% FCS and 100 ng/ml VEGF was partially blocked (30%) by the electroporation of either siRNA SEQ ID NO. 37 or the anti-KDR siRNA (FIGS. 24 and 25).

iv) Wound-Healing Studies.

(1) Set-up Assay.

Cells were plated at a density of 50.000 cells/well in 96-well plates coated with 1% gelatin and cultured in basal medium for 24 h. Thereafter, a lesion was performed by scraping off a narrow area of the culture and 10 ng/ml VEGF was added to the culture. The areas immediately after and 24 h after performing the lesion were measured and compared by means of the NIH ImageJ software. The percentage of healed area was quantified as follows:

Wound Healing (%)=Final Area/Initial area×100

Figure 26:
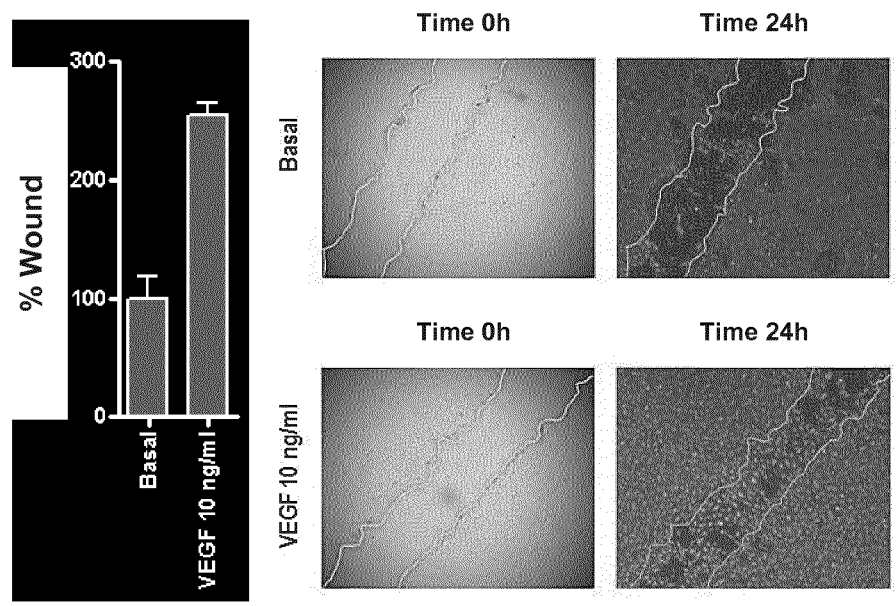
FIG. 26: A. quantification of wound healing in basal conditions and in response to 10 ng/ml VEGF. B. Pictures of the lesion at the time at time 0 and 24 h after induction.

As FIG. 26 shows, 10 ng/ml VEGF induced an increase of 2.5 fold in the rate of wound healing compared to the non-treated condition.

(2) Efficacy of siRNA SEQ ID NO. 37.

Cells were electropored and allowed to recover over a period of 24 h, thereafter cells were plated at a density of 70.000 cells/well in 96-well plates coated with 1% gelatin. 24 h after plating lesions were induced by scraping off a narrow area of cells and cultures were analyzed 16 h after induction of lesions. The analysis was performed by staining cells with 10 µM calceine-AM and analyzing the areas scraped and the percentage of area that was covered by cells again. All the conditions tested were assayed in the presence of basal medium and complete medium (supplemented with 10% FCS and 100 ng/ml VEGF). The conditions tested were as follows and migration was analyzed 24 h after plating:
  Non-transfected cells
  Sham electroporated cells
  Cells transfected with 1 µM siRNA anti-KDR (Life Technologies, Ref: 145034)
  Cells transfected with 1 µM siRNA SEQ ID NO. 37.

Figure 27:
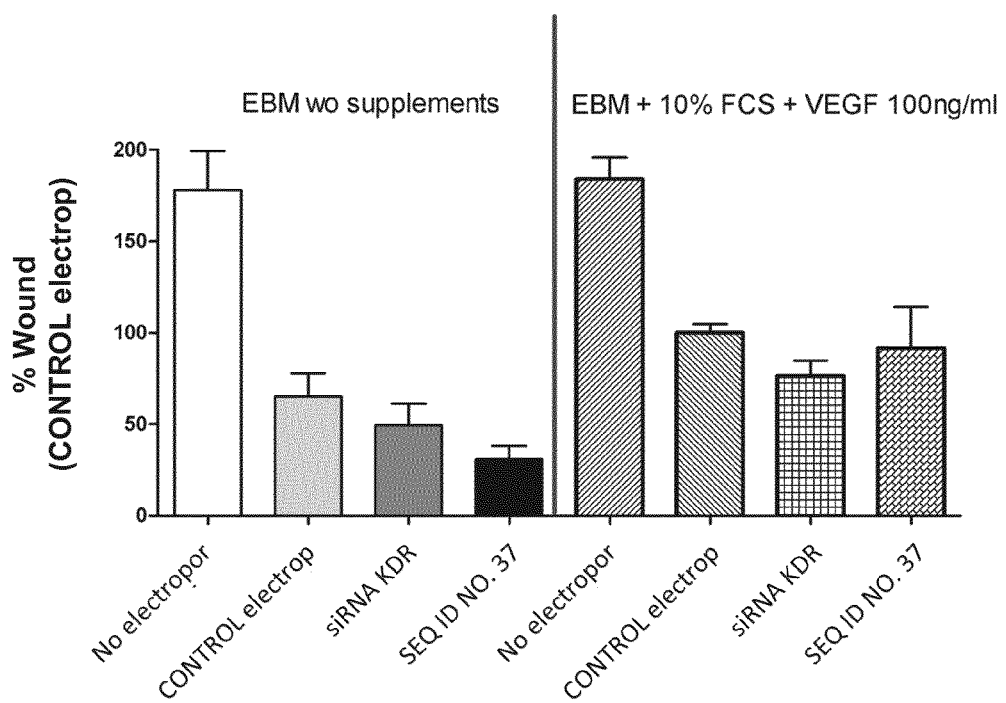
FIG. 27: Quantification of wound healing in basal conditions and in response to complete medium (10% FCS and 100 ng/ml VEGF)
Figure 28:
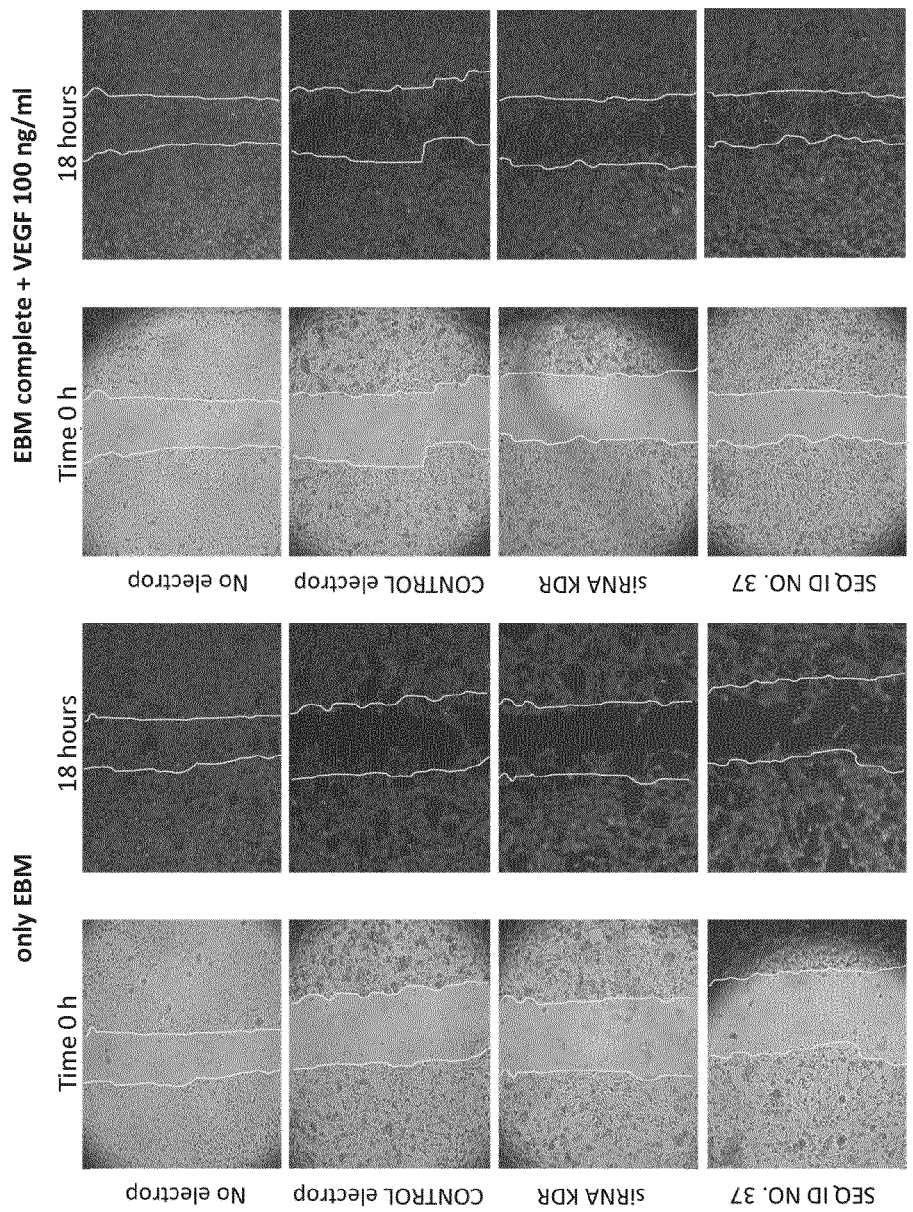
FIG. 28: Pictures showing the wounds at time 0 and 16 h after induction in the different conditions assayed.
Figure 29:
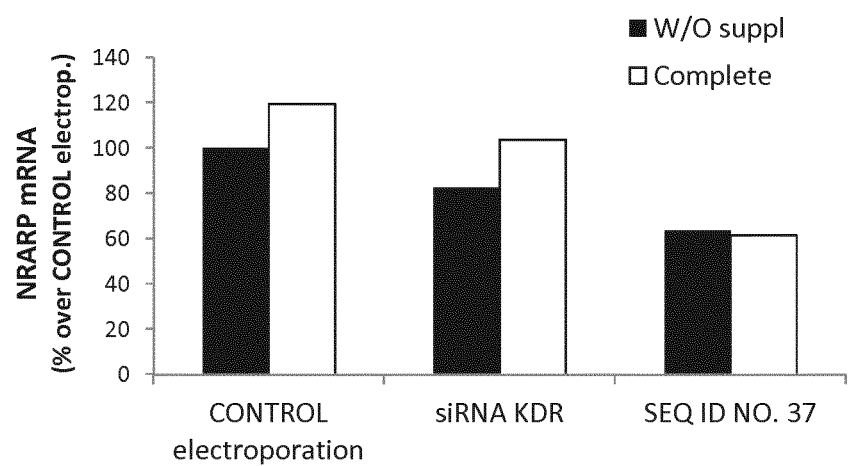
FIG. 29: mRNA levels of NRARP in HUVEC cells.

As in prior experiments, the results show a deleterious effect of electroporation on wound healing, for that reason all conditions were compared to the sham electroporated cells. As shown on FIGS. 27 and 28, siRNA SEQ ID NO. 37 very effectively reduced rate of wound healing in basal medium. The effect of siRNA SEQ ID NO. 37 was even greater than that of the positive control anti-KDR siRNA. This effect on wound healing is however masked when the cells are cultured in complete medium, most likely due to the potent effect of FCS on cell migration.

v) NRARP mRNA levels in cells from the above mentioned experiments. HUVEC cells from the above mentioned studies were collected and total RNA extracted to analyze by qPCR the levels of the NRARP target gene. FIG.

29 shows the reduction in NRARP mRNA levels in response to electroporation of siRNA SEQ ID NO. 37.

Taken together the results presented in the present study we can conclude that siRNA SEQ ID NO. 37 shows an antiantiogenic effect in HUVEC cells as shown by a reduction in proliferation, migration and formation of capillary structures.

2. In Vivo Analysis 2.1 Expression of NRARP in Retina and Choroid in a Rat Model of Choroidal Neovascularization Induced by LASER 2.1.1 Objective The objective of the present study was to assess the expression of NRARP at different time-points in the retina and choroid of Norway Brown Rats in which CNV had been induced by LASER. Analysis of the expression of this target gene served a double purpose i) to assess whether NRARP is up-regulated in response to CNV in order to study if the target is a candidate to be silenced with the aim of developing a new compound for the treatment of retinal diseases related to neovascularization ii) to study the temporary expression of NRARP to determine the best time to treat the animals in order to silence the target gene.

2.1.2 Introduction

CNV is a non-specific lesion common to several chorioretinal diseases. These lesions are characterized by a sequence of events that entail a break or disruption of Brunch's membrane, induction of inflammation and angiogenesis with invasion of choriocapillary endothelial cells, perycites and inflammatory cells into the subretinal space and/or subretinal pigment epithelium {Grossniklaus H E et al 2010}. The penetration of choriocapillaries into the subretinal space in a common hallmark of several retinal diseases. Some example of these diseases include AMD, PDR or DRE.

CNV can be induced in animal models by inducing a lesion in Brunch's membrane; this lesion initiates the molecular events leading to a full blown CNV characterized by increased angiogenic factors and inflammatory mediators.

We have used the laser-induced CNV model in Brown Norway rats validated at EyeCRO to analyze the expression of selected targets at different time-points after induction of the lesions. For this purpose three lesions were induced in each eye of 18 animals that were subsequently sacrificed and eyes collected and sent to Sylentis for further analysis. The target analyzed was NRARP. NRARP is a glycoprotein related to activation of vascular endothelial cells. The gene is overexpressed in a whole range of cancers and its overexpression correlates with metastasis and short survival rate. Furthermore, expression levels of this gene in human breast cancer correlate with blood vessel formation and the protein encoded by this gene has been found to have a role in endothelial cell migration and vasculature generation independent of VEGF {Faibish M R et al. 2011}.

2.1.3 Methods i) Animals

TABLE 1

| Animals | |
|---|---|
| Species | Rat |
| Strain | Brown Norway |
| Supplier | Charles River Laboratories |
| Number and sex | 18 Females |
| Age range at induction | 6-8 weeks |

TABLE 1-continued

| Animals | |
|---|---|
| Species | Rat |
| Randomization and allocation to treatment groups | Animals were randomly assigned to the different experimental |
| Identification | Ear tag |
| Housing | Animals were housed in groups of 3, under standard conditions. |
| Environment conditions, bedding, water and diet | Under controlled (lighting, temperature and humidity) conditions. Standard diet and tap water ad libitum. | ii) Experimental Groups

TABLE 2

| Experimental groups | | | | |
|---|---|---|---|---|
| Group | Number of animals | Induction | Assessment | Time of tissue collection |
| 1 | 3 | None | Enucleation of eyes and individual collection of retina and RPE/choroid | — |
| 2 | 3 | Laser CNV 3 lesions/eye, bilateral | | 6 h |
| 3 | 3 | | | 24 h |
| 4 | 3 | | | 72 h |
| 5 | 3 | | | 168 h |
| 6 | 3 | | | 504 h | iii) Exclusion Criteria

Any eyes where hemorrhage is apparent in ≥2 out of 3 laser lesions immediately following laser application.

All tissue samples were placed in criotubes appropriately identified, and immediately frozen in liquid nitrogen. Criotubes were identified with the experimental condition and shipped on dry ice to Sylentis.

iv) Analysis of Target Gene Expression (1) RNA Isolation and Retrotranscription

Total RNA was isolated from retina and choroid using RNeasy RNA extraction kit (Invitrogen, Calif., USA). 4 µg of total RNA were retrotranscribed using High-Capacity cDNA Archive kit (Applied Biosystems, Inc., Foster City, Calif., USA) according to the manufacturer's instructions.

(2) qPCR qPCR was performed using Stepone plus detection system (Applied Biosystems). 500 nanograms of each sample were amplified in a TaqMan 2× Universal Master Mix under the following conditions: 95° C. for 10 min, followed by 40 cycles of 95° C. for 15 s and 60° C. for 1 min. All qPCR amplifications were performed in triplicate and repeated in at least two independent experiments, always including reverse transcription controls and no template controls.

2.1.4 Results—Expression of NRARP

Figure 14:
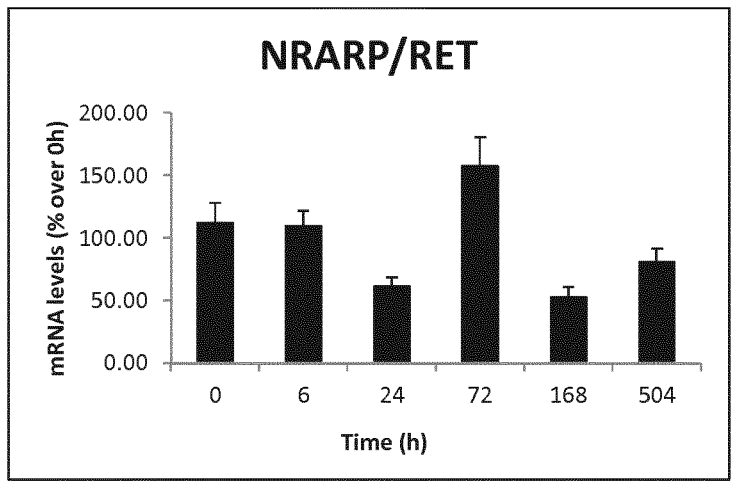
FIG. 14: Levels of NRARP mRNA in the retina following induction of CNV by laser. Data represent means±s.e.m of three animals (six eyes) per time-point.
Figure 15:
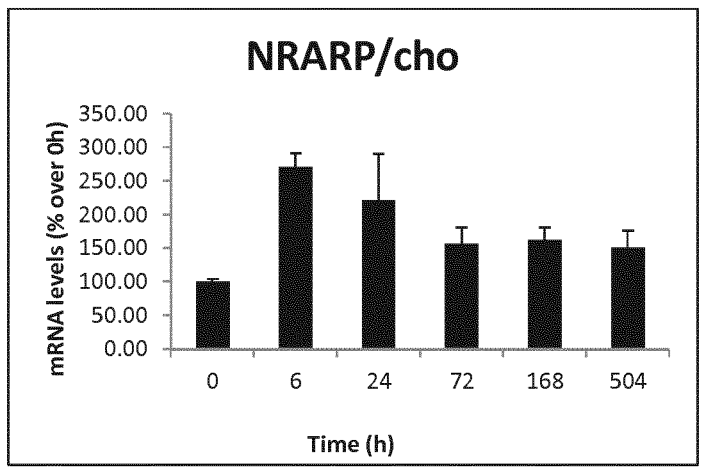
FIG. 15: Levels of NRARP mRNA in choroid/RPE following induction of CNV by laser. Data represent means±s.e.m of at least two animals (four eyes) per time-point.

Expression of NRARP was analyzed in the retina and in the RPE/Choroid at different time-points following induction of CNV by laser. The results obtained show a slight decrease in NRARP mRNA levels in the retina 24 h after induction of laser lesions. 72 h after induction of lesions the levels of NRARP mRNA increase slightly (1.5 fold over time=0). At the end of the study (t=504 h) levels of NRARP were equivalent to those observed prior to induction of lesions (FIG. 14)

mRNA levels of NRARP were drastically up-regulated in the choroid/RPE 6 h after induction of CNV (~2.7 fold) and slowly started to decrease thereafter. Basal levels were not recovered within the time-frame of the study (FIG. 15).

2.1.5 Conclusions

Taking together the results of this study it can be concluded that NRARP is an effective target against which a treatment to control neovascularization in the retina can be developed. The pattern of expression in both retina and choroid indicate that it might be a good candidate to silence given the significant induction of its expression in the model used in this study and its role in angiogenesis.

2.2 Evaluation of siRNA Targeting NRARP on Reduction of Lesion Size and Leakage in a Rat Model of Laser-Induced Choroidal Neovascularization.

2.2.1 Objective

To determine the anti-angiogenic/vascular disrupting effects of one test agent (siRNA SEQ ID NO.37) after topical administration in a rat model of laser-induced choroidal neovascularization (laser CNV).

2.2.2 Summary of the Study

A 26 day study was conducted with female Brown Norway rats to determine the anti-angiogenic/vascular disrupting effects of topical instillation of SEQ ID NO: 37 in a laser induced model of choroidal neovascularization.

A total of 18 rats were divided into 3 groups of 6 rats per group. On Days 1-26, Groups 1 and 3 received topical instillation once a day of vehicle (Group 1), or 5 mg/ml SEQ ID NO: 37 (Group 3). On Day 7, Group 3 received bilateral intravitreal injection of 5 µg/eye anti-VEGF (positive control).

On Day 3, laser treatments were performed using a 520 nm thermal laser to generate a total of three lesions per eye.

On Day 26 (3-weeks post-laser treatment), fluorescein angiography was performed and lesion size area was determined using image analysis software (ImageJ). Rats receiving either 5 µg/eye anti-VEGF Ab, or topical instillation of 5 mg/ml SEQ ID NO: 37, showed a significant reduction in lesion size compared to their respective vehicle control group.

2.2.3 Materials and Methods 2.2.3.1 Laser-induced Choroidal Neovascularization (CNV) in rats Days 1-26: Topical instillation of vehicle or test agent, QD (Arms 1, 2)

Day 5: Bilateral Laser treatment to produce 3 lesions per eye

Day 7: Bilateral intravitreal injection of positive control (Arm 3)

Day 26: In-vivo fluorescein angiography

Day 26: Enucleation of eyes and individual collection of retina and RPE/choroid Study Arms 2.2.3.2 Study Arms

TABLE 3

Arm Allocation

| Arm | Induction | Treatment | Treatment Details | Assessment |
|---|---|---|---|---|
| 1 | Laser CNV 3 lesions/eye, bilateral | PBS (n = 6 rats) | Topical instillation on Days 1-26, QD | In-vivo fluorescein angiography on Day 26; Enucleation of eyes and individual collection of retina and RPE/choroid on Day 26 |
| 2 | Laser CNV 3 lesions/eye, bilateral | SEQ ID NO. 37 5 mg/ml (n = 6 rats) | Topical instillation on Days 1-26, QD | |
| 3 | Laser CNV 3 lesions/eye, bilateral | Anti-VEGF Ab R&D systems AF564, 5 µg/eye (n = 6 rats) | Bilateral intravitreal injection on Day 7 | |

2.2.3.3 Animals

Strain: Brown Norway

Sex: Female

Age Range: 6-8 weeks old

Weight Range: 120-150 g

Supplier: Charles River Laboratories

Number of Study Animals: 18

2.2.3.4 Housing Requirements

All animals were housed in groups of 3 in large cages kept in ventilated shelves under standard animal care conditions.

2.2.3.5 Formulation Preparation and Storage

USP (U.S. Pharmacopoeia) materials and sterile vessels were utilized for all formulations, using the following aliquots of the test material:

Topical Vehicle-26 aliquots/130 µl each+2 extra. siRNA SEQ ID NO.37 5 mg/ml-26 aliquots/130 µl each+2 extra.

All formulations were stored at 4±3° C.

2.2.3.6 Anesthesia

Ketamine and Xylazine were mixed using a U-100 syringe utilizing 20 units of Ketamine (100 mg/ml) and 100 unite of Xylazine (20 mg/ml). The anesthesia mixture was applied via intraperitoneal (IP) injection at 1 µl/g (body weight).

2.2.3.7 Laser Application to Produce CNV Lesions

Animal eyes were dilated with 1% Cyclogyl solution and protected from light. Following observable dilation, the animals were sedated with ketamine/xylazine. The fundus of sedated animals was observed and recorded using a Micron III small animal funduscope (Phoenix Research). Laser treatments were performed using a thermal laser connected through the Micron III custom laser attachment. A total of 3 lesions per eye were placed per eye using a wavelength of 520 nm. The resultant fundus images were recorded and evaluated to confirm that the laser has successfully produced a bubble through the Bruch's membrane.

2.2.3.8 Intravitreal Administration

Animals were anesthetized with ketamine/xylazine and pupils were dilated with topical administration of Cyclogyl and/or Tropicamide. Following sedation and dilation, a total volume of 5 µl per eye was injected into the vitreous at the pars plana using a Hamilton syringe and a 33 gauge needle.

2.2.3.9 Exclusions

Any eyes displaying signs of hemorrhage following laser application or intravitreal injection were excluded from analysis.

2.2.3.10 Fluorescein Angiography

Animals were anesthetized with ketamine/xylazine and then received an IP injection of 10% fluorescein sodium at 1 µl/gram of body weight. Fundus images were captured as 8-bit TIFF files using the Micron III and exciter/barrier filters for a target wavelength of 488 nm. Standard color fundus photos were also captured for each eye.

2.2.3.11 Imaging and Lesion Quantification

All TIFF images were quantified using computerized image-analysis software (ImageJ, NIH, USA). Lesions were individually traced free-hand in order to quantify the area in pixels and the color fundus photos were used as a reference for lesion location. Areas of avascularization in the center of lesions were excluded from area calculations. If there was hemorrhage or two lesions overlapping, these lesions were excluded from analysis.

2.2.3.12 Tissue Collection

Animals were anesthetized with ketamine/xylazine (80/10 mg/kg) and then euthanized by IP administration of Euthasol (pentobarbital) at 200 mg/kg. Following euthanization, the eyes were enucleated and individually fixed in 4% paraformaldehyde. Following fixation, all eyes were stored in individual 2 mL screw cap polypropylene tubes.

2.2.3.13 Statistical Analyses

Statistical Analyses was performed with Graphpad Prism software (version 4.0) using a two-tailed Mann-Whitney t-test. Only changes with a p-value 0.05 are deemed statistically significant.

2.2.4 Results

The effect of topical instillation administration of SEQ ID NO:

37 was evaluated in a rat model of laser-induced CNV. At 3 weeks post laser treatment, fluorescein angiography was performed to quantify the size (area in pixels) of the CNV lesion in the rat eyes.

Topical application of 5 mg/ml of SEQ ID NO: 37 reduced lesion size in rat eyes relative to vehicle instillation alone. The difference in average lesion size relative to the vehicle group was significant (FIG. 16; *, $p \leq 0.05$, unpaired t-test with two-tailed Mann-Whitney post-test).

Figure 16:
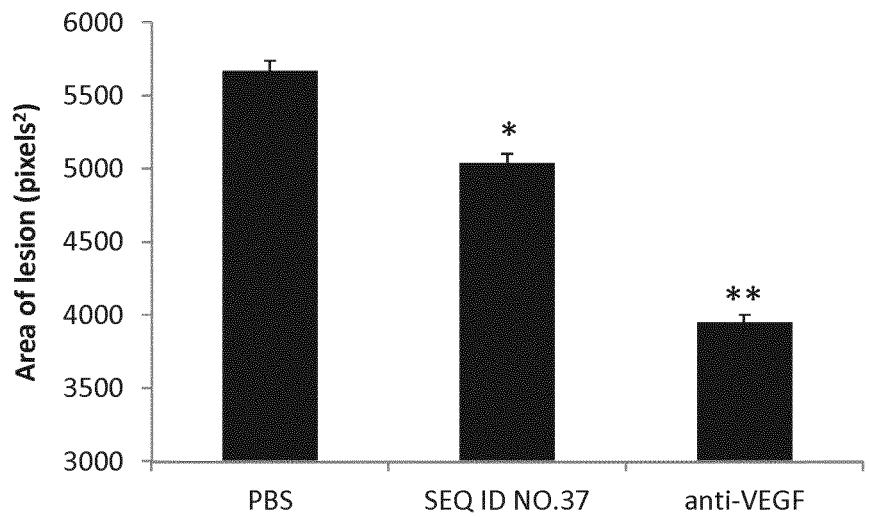
FIG. 16: Bar graph of lesion measurements at three weeks post laser treatment either with vehicle or SEQ ID NO.37 (5 mg/mL) topically administered, or with intravitreal injection of anti-VEGF (5 µg/eye). Areas of the lesions were determined by fluorescein angiography which were quantified (in $pixels^2$) using computerized image-analysis software excluding the avascularization area in the center of the lesion. Data represent means±s.e.m of six animals (twelve eyes) per time-point.

Bilateral intravitreal injection of the positive control, anti-VEGF, significantly reduced lesion size relative to control (FIG. 16; **, $p \leq 0.01$, unpaired t-test with two-tailed Mann-Whitney post-test).

2.2.5 Conclusions

In a rat model of choroidal neovascularization, topical instillation of 5 mg/ml SEQ ID NO.37 significantly reduces lesion size relative to topical instillation of the vehicle alone.

REFERENCES

Angaji S. A, Hedayati S. S, Poor R. H, et al. "Application of RNA interference in treating human diseases" *J Genet.* 2010. Vol. 89. 4. 527-37.

Bird A C. "Therapeutic targets in age-related macular disease". *J Clin Invest.* 2010 September; 120(9):3033-41.

Bramsen J. B., Laursen M. B., Nielsen A. F., et al. "A large-scale chemical modification screen identifies design rules to generate siRNAs with high activity, high stability and low toxicity" *Nucleic Acids Res* 2009 Vol. 37 Issue: 9 Pages: 2867-81.

Campochiaro P A. "Potential applications for RNAi to probe pathogenesis and develop new treatments for ocular disorders". *Gene Ther.* 2006 March; 13(6):559-62.

Cerutti, L., N. Mian, et al. "Domains in gene silencing and cell differentiation proteins: the novel PAZ domain and redefinition of the Piwi domain." Trends Biochem Sci. 2000 25(10): 481-2.

Collins, R. E. and X. Cheng. "Structural domains in RNAi."*FEBS Lett* 2005 579(26): 5841-9.

Chang C. I, Kim H. A, Dua P, et al. "Structural Diversity Repertoire of Gene Silencing Small Interfering RNAs" Nucleic Acid Ther. 2011. Vol. 21. 3. 125-31.

Chong R H, Gonzalez-Gonzalez E, et al. "Gene silencing following siRNA delivery to skin via coated steel microneedles: In vitro and in vivo proof-of-concept". *J Control Release* 2013, 166:211-9.

Del Amo E M and Urtti A. "Current and future ophthalmic drug delivery systems. A shift to the posterior segment". *Drug Discov Today* 2008, 13:135-143.

Deleavey G. F and Damha M. J. "Designing chemically modified oligonucleotides for targeted gene silencing". *Chem Biol.* 2012 Vol. 19.8. 937-54.

Duvvuri S, Majumdar S, Mitra A K. "Drug delivery to the retina: challenges and opportunities". *Expert Opin Biol Ther* 2003, 3:45-56.

Edelhauser H F, Rowe-Rendleman C L, Robinson M R, Dawson D G, et al. "Ophthalmic drug delivery systems for the treatment of retinal diseases: basic research to clinical applications". *Invest Ophthalmol Vis Sci* 2010, 51:5403-5420.

Elbashir, S. M., W. Lendeckel, et al. "RNA interference is mediated by 21- and 22-nucleotide RNAs." *Genes Dev.* 2001 15(2): 188-200.

Faibish M, Francescone R, Bentley B, et al. "A YKL-40-Neutralizing Antibody Blocks Tumor Angiogenesis and Progression: A Potential Therapeutic Agent in Cancers". *Mol Cancer Ther* 2011; 10:742-751.

Fire A, Xu S, et al. "Potent and specific genetic interference by double-stranded RNA in *Caenorhabditis elegans.*" *Nature.* 1998 391(6669): 806-11.

Grossniklaus H E, Kang S J, et al. "Animal models of choroidal and retinal neovascularization" *Prog Retin Eye Res* 2010 29(6): 500-19.

Guzman-Aranguez A, Loma P and Pintor J. "Small-interfering RNAs (siRNAs) as a promising tool for ocular therapy". *British Journal of Pharmacology.* 2013. 170 730-747.

Hutvagner G, and Zamore P D. "A microRNA in a multiple-turnover RNAi enzyme complex." *Science.* 2002. 297 (5589): 2056-60.

Kigasawa K, Kajimoto K, et al. "Noninvasive delivery of siRNA into the epidermis by iontophoresis using an atopic dermatitis-like model rat". *Int J Pharm* 2010, 383:157-60.

Kim D H, Behlke M A, Rose S D, et al. "Synthetic dsRNA Dicer substrates enhance RNAi potency and efficacy" *Nat Biotechnol* 2005. Vol. 23 Issue: 2 Pages: 222-6.

Kornbrust D, Cavagnaro J, Levin A, et al. "Oligo safety working group exaggerated pharmacology subcommittee consensus document" *Nucleic Acid Ther* 2013 Vol. 23, 1, Pag: 21-8.

Leachman S A, Hickerson R P, et al. "First-in-human mutation-targeted siRNA phase Ib trial of an inherited skin disorder". *Mol Ther* 2010, 18:442-6.

Lewis B P, Shih I, et al. "Prediction of mammalian micro RNA targets." *Cell.* 2003 115:787-798.

Liu J, Carmell M A, et al. "Argonaute2 is the catalytic engine of mammalian RNAi." *Science.* 2004 305(5689): 1437-41.

Livak K J and Schmittgen T D. "Analysis of relative gene expression data using real-time quantitative PCR and the 2(−Delta Delta C(T)) Method" *Methods.* 2001; Vol: 25, Issue: 4, Pages: 402-8.

Ma J B, Yuan Y R, et al. "Structural basis for 5′-end-specific recognition of guide RNA by the *A. fulgidus* Piwi.

Maniatis T, et al., Molecular Cloning: A Laboratory Manual, Cold Spring Harbor Laboratory, 1982, at pages 387-389.

Nakai N, Kishida T, et al. "Therapeutic RNA interference of malignant melanoma by electrotransfer of small interfering RNA targeting Mitf". *Gene Ther* 2007, 14:357-65.

Nykanen A, Haley B, et al. "ATP requirements and small interfering RNA structure in the RNA interference pathway." Cell 2001 107(3): 309-21.

Orban T I and Izaurralde E. "Decay of mRNAs targeted by RISC requires XRN1, the Ski complex, and the exosome." Rna. 2005 11(4): 459-69.

Phng L K, Potente M, et al. "Nrarp coordinates endothelial Notch and Wnt signaling to control vessel density in angiogenesis." *Dev Cell* 2009 16(1): 70-82.

Rand T A, Petersen S, et al. "Argonaute2 cleaves the anti-guide strand of siRNA during RISC activation." *Cell.* 2005 123(4): 621-9.

Rowe-Rendleman C L, Durazo S A, et al. "Drug and gene delivery to the back of the eye: from bench to bedside." *Investigative ophthalmology & visual science.* 2014 55(4): 2714-30.

Sanghvi Y S. "A status update of modified oligonucleotides for chemotherapeutics applications" *Curr Protoc Nucleic Acid Chem.* 2011 Vol. 4.411-22.

Song J J, Smith S K, et al. "Crystal structure of Argonaute and its implications for RISC slicer activity." *Science.* 2004 305(5689): 1434-7.

Walton S P, Wu M, Gredell J A and Chan C. "Designing highly active siRNAs for therapeutic applications" *FEBS J._2010.* Vol. 277. 23. 4806-13.

The invention claimed is:

1. A method of treating an eye condition characterized by increased expression and/or activity of NRARP in a subject in need thereof comprising administering to the subject a siRNA molecule that specifically targets at least one sequence selected from the group consisting of SEQ ID NO. 1 to SEQ ID NO. 9, wherein said siRNA comprises a 19- to 28-nucleotide double-stranded structure and wherein said siRNA comprises at least one sequence selected from the group consisting of SEQ ID NO. 10 to SEQ ID NO. 66.

2. The method according to claim 1, wherein said eye condition is related to neovascularization.

3. The method according to claim 2, wherein said eye condition is selected from age-related macular degeneration (AMD), ischemic retinopathy, diabetic macular edema (DME), proliferative diabetic retinopathy (PDR), diabetic retina ischemia (DRI), diabetic retinal edema (DRE), myopic neovascularization and retinopathy of prematurity (ROP) and combinations thereof.

4. The method according to claim 1 wherein said siRNA comprises a 19-nucleotide double-stranded region.

5. The method according to claim 4 wherein said siRNA is blunt-ended.

6. The method according to claim 1 wherein said siRNA comprises or consists of at least one sequence selected from the group consisting of SEQ ID NO. 10 to SEQ ID NO. 18.

7. The method according to claim 1, wherein said siRNA comprises or consists of a sense strand which comprises or consists of at least one sequence selected from the group consisting of SEQ ID NO. 10 to SEQ ID NO. 18, and an antisense strand which is complementary to the sense strand.

8. The method according to claim 1, wherein at least one nucleotide comprises a chemical modification.

9. The method according to claim 8 wherein said chemical modification of a nucleotide is selected from: 2'-O-methyl modification, 2'-fluoro modification, introduction of phosphorothioate modified nucleotides, substitution of uracil with 5-Propynyluracil, substitution of uracil with 5'-methyluridine, substitution of uracyl ribose nucleotides with 4'-thioribose and substitution of uracyl ribose nucleotides with deoxythymidine nucleotides and combinations thereof.

10. The method according to claim 9 wherein said chemical modification is on the sense strand, the antisense strand or on both.

11. The method according to claim 10 wherein said siRNA comprises at least one sequence selected from the group consisting of SEQ ID NO. 19-SEQ ID NO. 66.

12. The method according to claim 8, wherein said siRNA comprises or consists of a sense strand which comprises or consists of at least one sequence selected from the group consisting of SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63 and SEQ ID NO. 65, and an antisense strand which is complementary to the sense strand which is selected from the group consisting of SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64 and SEQ ID NO. 66.

13. A siRNA molecule wherein said molecule specifically targets at least one sequence selected from the group consisting of SEQ ID NO. 1 to SEQ ID NO. 9 and reduces expression of NRARP gene when introduced in a cell and wherein said siRNA comprises a 19- to 28-nucleotide blunt-ended double-stranded structure, wherein said siRNA comprises at least one sequence selected from the group consisting of SEQ ID NO. 10 to SEQ ID NO. 66.

14. The siRNA molecule according to claim 13, wherein at least one nucleotide comprises a chemical modification.

15. The siRNA molecule according to claim 14, wherein said chemical modification of a nucleotide is selected from: 2'-O-methyl modification, 2'-fluoro modification, introduction of phosphorothioate modified nucleotides, substitution of uracil with 5-Propynyluracil, substitution of uracil with 5'-methyluridine, substitution of uracyl ribose nucleotides with 4'-thioribose and substitution of uracyl ribose nucleotides with deoxythymidine nucleotides and combinations thereof.

16. The siRNA molecule according to claim 14 wherein said chemical modification is on the sense strand, the antisense strand or on both.

17. The siRNA molecule according to claim 13, wherein said siRNA comprises at least one sequence selected from the group consisting of SEQ ID NO. 19-SEQ ID NO. 66.

18. The siRNA molecule according to claim 13, wherein said siRNA comprises or consists of a sense strand which comprises or consists of at least one sequence selected from the group consisting of SEQ ID NO. 19, SEQ ID NO. 21, SEQ ID NO. 23, SEQ ID NO. 25, SEQ ID NO. 27, SEQ ID NO. 29, SEQ ID NO. 31, SEQ ID NO. 33, SEQ ID NO. 35, SEQ ID NO. 37, SEQ ID NO. 39, SEQ ID NO. 41, SEQ ID NO. 43, SEQ ID NO. 45, SEQ ID NO. 47, SEQ ID NO. 49, SEQ ID NO. 51, SEQ ID NO. 53, SEQ ID NO. 55, SEQ ID NO. 57, SEQ ID NO. 59, SEQ ID NO. 61, SEQ ID NO. 63 and SEQ ID NO. 65, and an antisense strand which is complementary to the sense strand which is selected from the group consisting of SEQ ID NO. 20, SEQ ID NO. 22, SEQ ID NO. 24, SEQ ID NO. 26, SEQ ID NO. 28, SEQ ID NO. 30, SEQ ID NO. 32, SEQ ID NO. 34, SEQ ID NO. 36, SEQ ID NO. 38, SEQ ID NO. 40, SEQ ID NO. 42, SEQ ID NO. 44, SEQ ID NO. 46, SEQ ID NO. 48, SEQ ID NO. 50, SEQ ID NO. 52, SEQ ID NO. 54, SEQ ID NO. 56, SEQ ID NO. 58, SEQ ID NO. 60, SEQ ID NO. 62, SEQ ID NO. 64 and SEQ ID NO. 66.

19. The siRNA molecule according to claim 18, wherein the sense strand comprises or consists of SEQ ID NO: 37 and the antisense strand comprises or consists of SEQ ID NO: 38.

20. The siRNA molecule according to claim 13, wherein the siRNA consists of a 19-nucleotide double-stranded structure.

21. A pharmaceutical composition wherein said composition comprises at least the siRNA molecule described in claim 19.

22. A siRNA molecule wherein said molecule specifically targets at least one sequence selected from the group consisting of SEQ ID NO. 1 to SEQ ID NO. 9, wherein said siRNA comprises a 19- to 28-nucleotide structure and wherein said siRNA comprises at least one sequence selected from the group consisting of SEQ ID NO. 10 to SEQ ID NO. 66.

23. The siRNA molecule according to claim 22 wherein said siRNA comprises or consists of at least one sequence selected from the group consisting of SEQ ID NO. 10 to SEQ ID NO. 18.

24. The siRNA molecule according to claim 23, wherein said siRNA comprises or consists of a sense strand which comprises or consists of at least one sequence selected from the group consisting of SEQ ID NO. 10 to SEQ ID NO. 18, and an antisense strand which is complementary to the sense strand.

25. The siRNA molecule according to claim 22, wherein the siRNA consists of a 19-nucleotide double-stranded structure.

26. A pharmaceutical composition wherein said composition comprises at least the siRNA molecule described in claim 22.

* * * * *

SEQUENCE LISTING

```
<160> NUMBER OF SEQ ID NOS: 66

<210> SEQ ID NO 1
<211> LENGTH: 19
<212> TYPE: DNA
<213> ORGANISM: Artificial Sequence
<220> FEATURE:
<223> OTHER INFORMATION: cDNA

<400> SEQUENCE: 1
caccaggaca tcgtgctct                                                  19

<210> SEQ ID NO 2
<211> LENGTH: 19
<212> TYPE: DNA
<213> ORGANISM: Artificial Sequence
<220> FEATURE:
<223> OTHER INFORMATION: cDNA

<400> SEQUENCE: 2
acatcgtgct ctatctcat                                                  19

<210> SEQ ID NO 3
<211> LENGTH: 19
<212> TYPE: DNA
<213> ORGANISM: Artificial Sequence
<220> FEATURE:
<223> OTHER INFORMATION: cDNA

<400> SEQUENCE: 3
aggacatcgt gctctatct                                                  19

<210> SEQ ID NO 4
<211> LENGTH: 19
<212> TYPE: DNA
<213> ORGANISM: Artificial Sequence
<220> FEATURE:
<223> OTHER INFORMATION: cDNA

<400> SEQUENCE: 4
gacatcgtgc tctatctca                                                  19

<210> SEQ ID NO 5
<211> LENGTH: 19
<212> TYPE: DNA
<213> ORGANISM: Artificial Sequence
<220> FEATURE:
<223> OTHER INFORMATION: cDNA

<400> SEQUENCE: 5
tgctctatct catcaccaa                                                  19

<210> SEQ ID NO 6
<211> LENGTH: 19
<212> TYPE: DNA
```

```
<213> ORGANISM: Artificial Sequence
<220> FEATURE:
<223> OTHER INFORMATION: cDNA

<400> SEQUENCE: 6
ccaggacatc gtgctctat                                                19

<210> SEQ ID NO 7
<211> LENGTH: 19
<212> TYPE: DNA
<213> ORGANISM: Artificial Sequence
<220> FEATURE:
<223> OTHER INFORMATION: cDNA

<400> SEQUENCE: 7
atcgtgctct atctcatca                                                19

<210> SEQ ID NO 8
<211> LENGTH: 19
<212> TYPE: DNA
<213> ORGANISM: Artificial Sequence
<220> FEATURE:
<223> OTHER INFORMATION: cDNA

<400> SEQUENCE: 8
gtgctctatc tcatcacca                                                19

<210> SEQ ID NO 9
<211> LENGTH: 19
<212> TYPE: DNA
<213> ORGANISM: Artificial Sequence
<220> FEATURE:
<223> OTHER INFORMATION: cDNA

<400> SEQUENCE: 9
accaggacat cgtgctcta                                                19

<210> SEQ ID NO 10
<211> LENGTH: 19
<212> TYPE: RNA
<213> ORGANISM: Artificial Sequence
<220> FEATURE:
<223> OTHER INFORMATION: siRNA sense strand

<400> SEQUENCE: 10
caccaggaca ucgugcucu                                                19

<210> SEQ ID NO 11
<211> LENGTH: 19
<212> TYPE: RNA
<213> ORGANISM: Artificial Sequence
<220> FEATURE:
<223> OTHER INFORMATION: siRNA sense strand

<400> SEQUENCE: 11
acaucgugcu cuaucucau                                                19

<210> SEQ ID NO 12
<211> LENGTH: 19
<212> TYPE: RNA
<213> ORGANISM: Artificial Sequence
<220> FEATURE:
<223> OTHER INFORMATION: siRNA sense strand

<400> SEQUENCE: 12
aggacaucgu gcucuaucu                                                19
```

```
<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
gacaucgugc ucuaucuca                                                    19

<210> SEQ ID NO 14
<211> LENGTH: 19
<212> TYPE: RNA
<213> ORGANISM: Artificial Sequence
<220> FEATURE:
<223> OTHER INFORMATION: siRNA

<400> SEQUENCE: 14
ugcucuaucu caucaccaa                                                    19

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
ccaggacauc gugcucuau                                                    19

<210> SEQ ID NO 16
<211> LENGTH: 19
<212> TYPE: RNA
<213> ORGANISM: Artificial Sequence
<220> FEATURE:
<223> OTHER INFORMATION: siRNA

<400> SEQUENCE: 16
aucgugcucu aucucauca                                                    19

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
gugcucuauc ucaucacca                                                    19

<210> SEQ ID NO 18
<211> LENGTH: 19
<212> TYPE: RNA
<213> ORGANISM: Artificial Sequence
<220> FEATURE:
<223> OTHER INFORMATION: siRNA

<400> SEQUENCE: 18
accaggacau cgugcucua                                                    19

<210> SEQ ID NO 19
<211> LENGTH: 22
<212> TYPE: RNA
<213> ORGANISM: Artificial Sequence
<220> FEATURE:
```

```
<223> OTHER INFORMATION: siRNA
<220> FEATURE:
<221> NAME/KEY: modified_base
<222> LOCATION: 1,3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 19
nannnangga nanngngcnn cn                                          22

<210> SEQ ID NO 20
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 2
<223> OTHER INFORMATION: /note="phosphothioate bond"
<220> FEATURE:
<221> NAME/KEY: modified_base
<222> LOCATION: 16,19
<223> OTHER INFORMATION: /mod_base="um"
<220> FEATURE:
<221> NAME/KEY: modified_base
<222> LOCATION: 18,20
<223> OTHER INFORMATION: /mod_base="gm"

<400> SEQUENCE: 20
angagcacga guccngnnn                                              20

<210> SEQ ID NO 21
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 21
nannnangga nanngngcnn cn                                          22

<210> SEQ ID NO 22
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 2
<223> OTHER INFORMATION: /note="phosphothioate bond"
<220> FEATURE:
<221> NAME/KEY: modified_base
```

```
<222> LOCATION: 16,19
<223> OTHER INFORMATION: /mod_base="OTHER"
      /note="uridine with 4'-thioribose modification"
<220> FEATURE:
<221> NAME/KEY: modified_base
<222> LOCATION: 17,20
<223> OTHER INFORMATION: /mod_base="gm"

<400> SEQUENCE: 22
angagcacga uguccnngnn                                                 20

<210> SEQ ID NO 23
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 23
nannnangga nanngngcnn cn                                              22

<210> SEQ ID NO 24
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 2
<223> OTHER INFORMATION: /note="phosphothioate bond"
<220> FEATURE:
<221> NAME/KEY: modified_base
<222> LOCATION: 16,19
<223> OTHER INFORMATION: /mod_base="OTHER"
      /note="5pU (5-Propynyluracile 3')"

<400> SEQUENCE: 24
angagcacga uguccnggng                                                 20

<210> SEQ ID NO 25
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 25
```
nannnangga nanngngcnn cn        22

<210> SEQ ID NO 26
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 15,18
<223> OTHER INFORMATION: /mod_base="OTHER"
      /note="5-methyluridine"
<220> FEATURE:
<221> NAME/KEY: modified_base
<222> LOCATION: 19
<223> OTHER INFORMATION: /mod_base="OTHER"
      /note="2'F Guanosine"

<400> SEQUENCE: 26
agagcacgau guccnggnn        19

<210> SEQ ID NO 27
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 27
nannnangga nanngngcnn cn        22

<210> SEQ ID NO 28
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 15,18
<223> OTHER INFORMATION: /mod_base="um"
<220> FEATURE:
<221> NAME/KEY: modified_base
<222> LOCATION: 17
<223> OTHER INFORMATION: /mod_base="gm"
<220> FEATURE:
<221> NAME/KEY: modified_base
<222> LOCATION: 19
<223> OTHER INFORMATION: /mod_base="OTHER"
      /note="2'F Guanosine"

<400> SEQUENCE: 28
agagcacgau guccngnnn        19

<210> SEQ ID NO 29
<211> LENGTH: 22
<212> TYPE: RNA
<213> ORGANISM: Artificial Sequence
<220> FEATURE:

```
<223> OTHER INFORMATION: siRNA
<220> FEATURE:
<221> NAME/KEY: modified_base
<222> LOCATION: 1
<223> OTHER INFORMATION: /mod_base="OTHER"
      /note="2'F cytidine"
<220> FEATURE:
<221> NAME/KEY: modified_base
<222> LOCATION: 3,5,11,14
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 13,16,19,22
<223> OTHER INFORMATION: /mod_base="um"

<400> SEQUENCE: 29
nannnangga nanngngcnn cn                                       22

<210> SEQ ID NO 30
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 15,18
<223> OTHER INFORMATION: /mod_base="um"
<220> FEATURE:
<221> NAME/KEY: modified_base
<222> LOCATION: 17
<223> OTHER INFORMATION: /mod_base="gm"
<220> FEATURE:
<221> NAME/KEY: modified_base
<222> LOCATION: 19
<223> OTHER INFORMATION: /mod_base="OTHER"
      /note="2'F Guanosine"

<400> SEQUENCE: 30
agagcacgau guccngnnn                                           19

<210> SEQ ID NO 31
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,4,9,12,16,18
<223> OTHER INFORMATION: /mod_base="cm"
<220> FEATURE:
<221> NAME/KEY: modified_base
<222> LOCATION: 11,14,17,19
<223> OTHER INFORMATION: /mod_base="um"

<400> SEQUENCE: 31
nannaggana nngngnnnn                                           19

<210> SEQ ID NO 32
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1
<223> OTHER INFORMATION: /mod_base="OTHER"
```

```
              /note="2'F Adenosine"
<220> FEATURE:
<221> NAME/KEY: modified_base
<222> LOCATION: 5
<223> OTHER INFORMATION: /mod_base="cm"
<220> FEATURE:
<221> NAME/KEY: modified_base
<222> LOCATION: 6
<223> OTHER INFORMATION: /mod_base="OTHER"
              /note="2'-o-methyladenosine"
<220> FEATURE:
<221> NAME/KEY: modified_base
<222> LOCATION: 10,15,18
<223> OTHER INFORMATION: /mod_base="um"

<400> SEQUENCE: 32
ngagnncgan guccnggng                                                      19

<210> SEQ ID NO 33
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1
<223> OTHER INFORMATION: /mod_base="OTHER"
              /note="2'F Cytidine"
<220> FEATURE:
<221> NAME/KEY: modified_base
<222> LOCATION: 3,4,9,12,16,18
<223> OTHER INFORMATION: /mod_base="cm"
<220> FEATURE:
<221> NAME/KEY: modified_base
<222> LOCATION: 11,14,17,19
<223> OTHER INFORMATION: /mod_base="um"

<400> SEQUENCE: 33
nannaggana nngngnnnn                                                      19

<210> SEQ ID NO 34
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,6
<223> OTHER INFORMATION: /mod_base="OTHER"
              /note="2'-o-methyladenosine"
<220> FEATURE:
<221> NAME/KEY: modified_base
<222> LOCATION: 5
<223> OTHER INFORMATION: /mod_base="cm"
<220> FEATURE:
<221> NAME/KEY: modified_base
<222> LOCATION: 10,15,18
<223> OTHER INFORMATION: /mod_base="um"

<400> SEQUENCE: 34
ngagnncgan guccnggng                                                      19

<210> SEQ ID NO 35
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 20,21
```

```
<223> OTHER INFORMATION: /mod_base="OTHER"
     /note="deoxithymine (2'H thymine)"

<400> SEQUENCE: 35
caccaggaca ucgugcucun n                                              21

<210> SEQ ID NO 36
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 20,21
<223> OTHER INFORMATION: /mod_base="OTHER"
     /note="deoxithymine (2'H thymine)"

<400> SEQUENCE: 36
agagcacgau guccuggugn n                                              21

<210> SEQ ID NO 37
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,4,12,16,18
<223> OTHER INFORMATION: /mod_base="cm"
<220> FEATURE:
<221> NAME/KEY: modified_base
<222> LOCATION: 2,8,10
<223> OTHER INFORMATION: /mod_base="OTHER"
     /note="2'-o-methyladenosine"
<220> FEATURE:
<221> NAME/KEY: modified_base
<222> LOCATION: 3,9
<223> OTHER INFORMATION: /mod_base="OTHER"
     /note="2'F Cytidine"
<220> FEATURE:
<221> NAME/KEY: modified_base
<222> LOCATION: 5
<223> OTHER INFORMATION: /mod_base="OTHER"
     /note="2'F Adenosine"
<220> FEATURE:
<221> NAME/KEY: modified_base
<222> LOCATION: 6
<223> OTHER INFORMATION: /mod_base="gm"
<220> FEATURE:
<221> NAME/KEY: modified_base
<222> LOCATION: 7,13,15
<223> OTHER INFORMATION: /mod_base="OTHER"
     /note="2'F Guanosine"
<220> FEATURE:
<221> NAME/KEY: modified_base
<222> LOCATION: 11,17,19
<223> OTHER INFORMATION: /mod_base="OTHER"
     /note="2'F Uridine"
<220> FEATURE:
<221> NAME/KEY: modified_base
<222> LOCATION: 14
<223> OTHER INFORMATION: /mod_base="um"

<400> SEQUENCE: 37 nnnnnnnnn nnnnnnnnn                                                  19

<210> SEQ ID NO 38
<211> LENGTH: 19
<212> TYPE: RNA
<213> ORGANISM: Artificial Sequence
<220> FEATURE:
```

```
<223> OTHER INFORMATION: siRNA
<220> FEATURE:
<221> NAME/KEY: modified_base
<222> LOCATION: 1,6
<223> OTHER INFORMATION: /mod_base="OTHER"
      /note="2'F Adenosine"
<220> FEATURE:
<221> NAME/KEY: modified_base
<222> LOCATION: 2,4,8,16
<223> OTHER INFORMATION: /mod_base="OTHER"
      /note="2'F Guanosine"
<220> FEATURE:
<221> NAME/KEY: modified_base
<222> LOCATION: 3,9
<223> OTHER INFORMATION: /mod_base="OTHER"
      /note="2'-o-methyladenosine"
<220> FEATURE:
<221> NAME/KEY: modified_base
<222> LOCATION: 5,7,13
<223> OTHER INFORMATION: /mod_base="cm"
<220> FEATURE:
<221> NAME/KEY: modified_base
<222> LOCATION: 10,12,18
<223> OTHER INFORMATION: /mod_base="OTHER"
      /note="2'F Uridine"
<220> FEATURE:
<221> NAME/KEY: modified_base
<222> LOCATION: 11,17,19
<223> OTHER INFORMATION: /mod_base="gm"
<220> FEATURE:
<221> NAME/KEY: modified_base
<222> LOCATION: 14
<223> OTHER INFORMATION: /mod_base="OTHER"
      /note="2'F Cytidine"
<220> FEATURE:
<221> NAME/KEY: modified_base
<222> LOCATION: 15
<223> OTHER INFORMATION: /mod_base="um"

<400> SEQUENCE: 38 nnnnnnnnn nnnnnnnnn                                                 19

<210> SEQ ID NO 39
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,3,4,9,12,16,18
<223> OTHER INFORMATION: /mod_base="cm"
<220> FEATURE:
<221> NAME/KEY: modified_base
<222> LOCATION: 11,14,17,19
<223> OTHER INFORMATION: /mod_base="um"

<400> SEQUENCE: 39
nannaggana nngngnnnn                                                19

<210> SEQ ID NO 40
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 5
<223> OTHER INFORMATION: /mod_base="cm"

<400> SEQUENCE: 40
agagnacgau guccuggug                                                19
```

```
<210> SEQ ID NO 41
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 16
<223> OTHER INFORMATION: /mod_base="um"

<400> SEQUENCE: 41
acanucngug cucuancucn au                                          22

<210> SEQ ID NO 42
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 15
<223> OTHER INFORMATION: /mod_base="gm"
<220> FEATURE:
<221> NAME/KEY: modified_base
<222> LOCATION: 17,19
<223> OTHER INFORMATION: /mod_base="um"

<400> SEQUENCE: 42
augagauaga gcacnangn                                              19

<210> SEQ ID NO 43
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 9,14,16
<223> OTHER INFORMATION: /mod_base="um"

<400> SEQUENCE: 43
ananucngng cucnancunn au                                          22

<210> SEQ ID NO 44
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 15
<223> OTHER INFORMATION: /mod_base="gm"
<220> FEATURE:
<221> NAME/KEY: modified_base
<222> LOCATION: 17,19
<223> OTHER INFORMATION: /mod_base="um"
```

<400> SEQUENCE: 44
augagauaga gcacnangn                                                           19

<210> SEQ ID NO 45
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 9,14,16
<223> OTHER INFORMATION: /mod_base="um"

<400> SEQUENCE: 45
ananucngng cucnancunn au                                                       22

<210> SEQ ID NO 46
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 17,19
<223> OTHER INFORMATION: /mod_base="OTHER"
      /note="5pU (5-Propynyluracile 3')"

<400> SEQUENCE: 46
augagauaga gcacgangn                                                           19

<210> SEQ ID NO 47
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 9,14,16
<223> OTHER INFORMATION: /mod_base="um"

<400> SEQUENCE: 47
ananucngng cucnancunn au                                                       22

<210> SEQ ID NO 48
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_feature

```
<222> LOCATION: 2
<223> OTHER INFORMATION: /note="phosphothioate bond"
<220> FEATURE:
<221> NAME/KEY: modified_base
<222> LOCATION: 18,20
<223> OTHER INFORMATION: /mod_base="OTHER"
      /note="uridine with 4'-thioribose modification"

<400> SEQUENCE: 48
anugagauag agcacgangn                                            20

<210> SEQ ID NO 49
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_feature
<222> LOCATION: 4,7,20
<223> OTHER INFORMATION: /note="phosphothioate bond"
<220> FEATURE:
<221> NAME/KEY: modified_base
<222> LOCATION: 9,14,16
<223> OTHER INFORMATION: /mod_base="um"

<400> SEQUENCE: 49
ananucngng cucnancunn au                                         22

<210> SEQ ID NO 50
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 17,19
<223> OTHER INFORMATION: /mod_base="OTHER"
      /note="uridine with 4'-thioribose modification"
<220> FEATURE:
<221> NAME/KEY: modified_base
<222> LOCATION: 18
<223> OTHER INFORMATION: /mod_base="gm"

<400> SEQUENCE: 50
augagauaga gcacgannn                                             19

<210> SEQ ID NO 51
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_binding
<222> LOCATION: 4,7,20
<223> OTHER INFORMATION: /note="phosphothioate bond"
<220> FEATURE:
<221> NAME/KEY: modified_base
<222> LOCATION: 9,14,16
<223> OTHER INFORMATION: /mod_base="um"

<400> SEQUENCE: 51
```
ananucngng cucnancunn au    22

<210> SEQ ID NO 52
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,17,19
<223> OTHER INFORMATION: /mod_base="OTHER"
    /note="uridine with 4'-thioribose modification"
<220> FEATURE:
<221> NAME/KEY: modified_base
<222> LOCATION: 18
<223> OTHER INFORMATION: /mod_base="gm"

<400> SEQUENCE: 52
angagauaga gcacgannn    19

<210> SEQ ID NO 53
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,19
<223> OTHER INFORMATION: /mod_base="cm"
<220> FEATURE:
<221> NAME/KEY: misc_binding
<222> LOCATION: 4,7,20
<223> OTHER INFORMATION: /note="phosphothiate bond"
<220> FEATURE:
<221> NAME/KEY: modified_base
<222> LOCATION: 9,14,16
<223> OTHER INFORMATION: /mod_base="um"

<400> SEQUENCE: 53
ananucngng cucnancunn au    22

<210> SEQ ID NO 54
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 2
<223> OTHER INFORMATION: /note="phosphothiate bond"
<220> FEATURE:
<221> NAME/KEY: modified_base
<222> LOCATION: 18,20
<223> OTHER INFORMATION: /mod_base="OTHER"
    /note="5pU (5-Propynyluracile 3')"

<400> SEQUENCE: 54
anugagauag agcacgangn    20

<210> SEQ ID NO 55
<211> LENGTH: 22
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,6,13,17,19
<223> OTHER INFORMATION: /mod_base="cm"

```
<220> FEATURE:
<221> NAME/KEY: misc_binding
<222> LOCATION: 4,7,21
<223> OTHER INFORMATION: /note="phosphothiate bond"
<220> FEATURE:
<221> NAME/KEY: modified_base
<222> LOCATION: 5,9,12,14,16,18
<223> OTHER INFORMATION: /mod_base="um"

<400> SEQUENCE: 55
anannnngng cnnnannnna nu                                          22

<210> SEQ ID NO 56
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_binding
<222> LOCATION: 2
<223> OTHER INFORMATION: /note="phosphothiate bond"
<220> FEATURE:
<221> NAME/KEY: modified_base
<222> LOCATION: 18,20
<223> OTHER INFORMATION: /mod_base="OTHER"
      /note="5'methyluridine (5mU)"

<400> SEQUENCE: 56
anugagauag agcacgangn                                             20

<210> SEQ ID NO 57
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1
<223> OTHER INFORMATION: /mod_base="OTHER"
      /note="2'F Adenosine"
<220> FEATURE:
<221> NAME/KEY: modified_base
<222> LOCATION: 2,5,9,11,15,17
<223> OTHER INFORMATION: /mod_base="cm"
<220> FEATURE:
<221> NAME/KEY: modified_base
<222> LOCATION: 4,7,10,12,14,16,19
<223> OTHER INFORMATION: /mod_base="um"

<400> SEQUENCE: 57
nnanngngnn nnannnnan                                              19

<210> SEQ ID NO 58
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,7,17,19
<223> OTHER INFORMATION: /mod_base="um"

<400> SEQUENCE: 58
angaganaga gcacgangn                                              19

<210> SEQ ID NO 59
<211> LENGTH: 19
<212> TYPE: RNA
```

```
<213> ORGANISM: Artificial Sequence
<220> FEATURE:
<223> OTHER INFORMATION: siRNA
<220> FEATURE:
<221> NAME/KEY: modified_base
<222> LOCATION: 1
<223> OTHER INFORMATION: /mod_base="OTHER"
      /note="2'-o-methyladenosine"
<220> FEATURE:
<221> NAME/KEY: modified_base
<222> LOCATION: 2,5,9,11,15,17
<223> OTHER INFORMATION: /mod_base="cm"
<220> FEATURE:
<221> NAME/KEY: modified_base
<222> LOCATION: 4,7,10,12,14,16,19
<223> OTHER INFORMATION: /mod_base="um"

<400> SEQUENCE: 59
nnanngngnn nnannnnan                                          19

<210> SEQ ID NO 60
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1
<223> OTHER INFORMATION: /mod_base="OTHER"
      /note="2'F Adenosine"
<220> FEATURE:
<221> NAME/KEY: modified_base
<222> LOCATION: 2,7,17,19
<223> OTHER INFORMATION: /mod_base="um"

<400> SEQUENCE: 60
nngaganaga gcacgangn                                          19

<210> SEQ ID NO 61
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 20,21
<223> OTHER INFORMATION: /mod_base="OTHER"
      /note="deoxithymine (2'H thymine)"

<400> SEQUENCE: 61
acaucgugcu cuaucucaun n                                       21

<210> SEQ ID NO 62
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 20,21
<223> OTHER INFORMATION: /mod_base="OTHER"
      /note="deoxithymine (2'H thymine)"

<400> SEQUENCE: 62
augagauaga gcacgaugun n                                       21

<210> SEQ ID NO 63
<211> LENGTH: 19
```

```
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 2,5,9,11,15,17
<223> OTHER INFORMATION: /mod_base="cm"
<220> FEATURE:
<221> NAME/KEY: modified_base
<222> LOCATION: 4,7,10,12,14,16,19
<223> OTHER INFORMATION: /mod_base="um"

<400> SEQUENCE: 63
ananngngnn nnannnnan                                              19

<210> SEQ ID NO 64
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 7
<223> OTHER INFORMATION: /mod_base="um"
<220> FEATURE:
<221> NAME/KEY: modified_base
<222> LOCATION: 12
<223> OTHER INFORMATION: /mod_base="cm"

<400> SEQUENCE: 64
augaganaga gnacgaugu                                              19

<210> SEQ ID NO 65
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,18
<223> OTHER INFORMATION: /mod_base="OTHER"
      /note="2'-o-methyladenosine"
<220> FEATURE:
<221> NAME/KEY: modified_base
<222> LOCATION: 2
<223> OTHER INFORMATION: /mod_base="cm"
<220> FEATURE:
<221> NAME/KEY: modified_base
<222> LOCATION: 3,13
<223> OTHER INFORMATION: /mod_base="OTHER"
      /note="2'F Adenosine"
<220> FEATURE:
<221> NAME/KEY: modified_base
<222> LOCATION: 4,10,12,14,16
<223> OTHER INFORMATION: /mod_base="um"
<220> FEATURE:
<221> NAME/KEY: modified_base
<222> LOCATION: 5,9,11,15,17
<223> OTHER INFORMATION: /mod_base="OTHER"
      /note="2'F Cytidine"
<220> FEATURE:
<221> NAME/KEY: modified_base
<222> LOCATION: 6,8
<223> OTHER INFORMATION: /mod_base="gm"
<220> FEATURE:
<221> NAME/KEY: modified_base
<222> LOCATION: 7,19
<223> OTHER INFORMATION: /mod_base="OTHER"
      /note="2'F Uridine"

<400> SEQUENCE: 65
```

```
nnnnnnnnnn nnnnnnnn                                                    19

<210> SEQ ID NO 66
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: modified_base
<222> LOCATION: 1,4,6,8,10,16
<223> OTHER INFORMATION: /mod_base="OTHER"
      /note="2'F Adenosine"
<220> FEATURE:
<221> NAME/KEY: modified_base
<222> LOCATION: 2
<223> OTHER INFORMATION: /mod_base="OTHER"
      /note="2'F Uridine"
<220> FEATURE:
<221> NAME/KEY: modified_base
<222> LOCATION: 3,5,9,11,15
<223> OTHER INFORMATION: /mod_base="gm"
<220> FEATURE:
<221> NAME/KEY: modified_base
<222> LOCATION: 7,17,19
<223> OTHER INFORMATION: /mod_base="um"
<220> FEATURE:
<221> NAME/KEY: modified_base
<222> LOCATION: 12
<223> OTHER INFORMATION: /mod_base="OTHER"
      /note="2'F Cytidine"
<220> FEATURE:
<221> NAME/KEY: modified_base
<222> LOCATION: 18
<223> OTHER INFORMATION: /mod_base="OTHER"
      /note="2'F Guanosine"

<400> SEQUENCE: 66
nnnnnnnnnn nnacnnnnn                                                   19
```